(12) United States Patent
Chiarello et al.

(10) Patent No.: US 9,227,924 B2
(45) Date of Patent: *Jan. 5, 2016

(54) PROCESSES FOR MAKING HYDRAZIDES

(71) Applicant: WYETH LLC, New York, NY (US)

(72) Inventors: George Anello Chiarello, Morrisonville, NY (US); Ayman Sahli, Amman (JO)

(73) Assignee: WYETH LLC, Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/504,738

(22) Filed: Oct. 2, 2014

(65) Prior Publication Data

US 2015/0099865 A1 Apr. 9, 2015

Related U.S. Application Data

(63) Continuation of application No. 13/755,886, filed on Jan. 31, 2013, now Pat. No. 8,853,451, which is a continuation of application No. 13/360,220, filed on Jan. 27, 2012, now Pat. No. 8,383,857, which is a continuation of application No. 12/123,777, filed on May 20, 2008, now Pat. No. 8,110,705.

(60) Provisional application No. 60/939,529, filed on May 22, 2007.

(51) Int. Cl.
C07C 241/04 (2006.01)
A61K 47/48 (2006.01)
C07C 319/20 (2006.01)

(52) U.S. Cl.
CPC ......... *C07C 241/04* (2013.01); *A61K 47/48715* (2013.01); *C07C 319/20* (2013.01)

(58) Field of Classification Search
CPC .......................... C07C 241/04; C07C 319/20
USPC .................................................. 564/149, 150
See application file for complete search history.

(56) References Cited

U.S. PATENT DOCUMENTS

| | | | |
|---|---|---|---|
| 4,291,022 A | 9/1981 | Sandrin et al. | |
| 4,479,953 A | 10/1984 | Friedman | |
| 4,671,958 A | 6/1987 | Rodwell | |
| 4,729,781 A | 3/1988 | Williams | |
| 4,859,233 A | 8/1989 | Williams | |
| 4,939,244 A | 7/1990 | Lee | |
| 4,970,198 A | 11/1990 | Lee et al. | |
| 5,053,394 A | 10/1991 | Ellestad et al. | |
| 5,079,233 A | 1/1992 | Lee | |
| 5,342,943 A | 8/1994 | Lau et al. | |
| 5,367,093 A | 11/1994 | Dekeyser et al. | |
| 5,635,603 A | 6/1997 | Hansen et al. | |
| 5,690,904 A | 11/1997 | MacWhorter et al. | |
| 5,750,470 A | 5/1998 | Morimoto et al. | |
| 5,770,701 A | 6/1998 | McGahren et al. | |
| 6,323,230 B1 | 11/2001 | Rossi | |
| 6,476,030 B1 | 11/2002 | Carling et al. | |
| 8,110,705 B2 * | 2/2012 | Chiarello et al. | 564/142 |
| 8,383,857 B2 * | 2/2013 | Chiarello et al. | 564/148 |
| 8,853,451 B2 * | 10/2014 | Chiarello et al. | 564/150 |
| 2003/0045546 A1 | 3/2003 | Cai et al. | |
| 2003/0060467 A1 | 3/2003 | Carling et al. | |
| 2003/0225155 A1 | 12/2003 | Fernandez-Pol et al. | |
| 2004/0127521 A1 | 7/2004 | Cai et al. | |
| 2004/0192900 A1 | 9/2004 | Kunz et al. | |
| 2008/0103113 A1 | 5/2008 | Hormann et al. | |

FOREIGN PATENT DOCUMENTS

| | | |
|---|---|---|
| DE | 2608336 | 9/1976 |
| JP | 2005-504014 | 2/2005 |
| JP | 2006-517964 | 8/2006 |
| KR | 10-2004-0004705 | 1/2004 |
| WO | WO 95/15769 | 6/1995 |
| WO | WO 2004/056369 | 7/2004 |
| WO | WO 2004/101512 | 11/2004 |
| WO | WO 2005/003099 | 1/2005 |
| WO | WO 2005/005378 | 1/2005 |
| WO | WO 2005/026123 | 3/2005 |
| WO | WO 2005/097119 | 10/2005 |
| WO | WO 2006/042240 | 4/2006 |

OTHER PUBLICATIONS

Akaji, K. et al. "Studies on Peptides. CXXVI 1'2 Synthesis of the Protected Tetracosapeptide Corresponding to Positions 30-53 of Mouse Epidermal Growth Factor (EGF)" *Chem. Pharm. Bull.* (1985) vol. 33, pp. 173-183.

Baltina, L. et al. "Lupane Triterpenes and Derivatives with Antiviral Activity" *Bioorganic & Medicinal Chemistry Letters* vol. 13 (2003) pp. 3549-3552.

(Continued)

*Primary Examiner* — Shailendra Kumar
(74) *Attorney, Agent, or Firm* — Womble Carlyle Sandridge & Rice, LLP

(57) ABSTRACT

A method is disclosed for preparing hydrazides from hydrazine and an acyl chloride which comprises the steps of (a) preparing a stirred substantially uniform slurry comprising hydrazine and an inert solvent at low temperature; and (b) adding an acyl chloride continuously to said slurry. The method avoids or limits production of undesired bis-hydrazide by-products. The method is used to prepare 3-methyl-3-mercaptobutanoic acid hydrazide, a molecule used to link calicheamicin to a monoclonal antibody.

28 Claims, 3 Drawing Sheets

(56) References Cited

OTHER PUBLICATIONS

L. Belec et al: "A study of the relationship between biological activity and propyl amide isomer geometry in oxytocin using 5-tert-butylproline to augment the Cys-Pro amide cis-isomer population." *J. Med. Chem* (2000) vol. 43 pp. 1448-1455.

Cerbai, G. et al. "Acidi Benzal-Bis-((3-Tio)-Propionici E Loro Derivati A Presunta Attivita' Antiprotozoaria E Antitubercolare" *Boll. Chim. Farm.* vol. 103 (1964) pp. 653-659.

Flekhter, 0. et al. "Synthesis and Antiviral Activity of Hydrazides and Substituted Benzalhydrazides of Betulinic Acid and Its Derivatives" *Russian Journal of Bioorganic Chemistry* vol. 29 (2003) pp. 296-301.

Fuji I, N. et al. "Total Synthesis of Bovine Pancreatic Ribonuclease A. Part 5.1 Synthesis of the Protected S-Protein (Positions 21-124) and the Protected S-Peptide (Positions 1-20)" Journal of the Chem. Soc. Perkin Transactions 1, (1981) pp. 819-830.

Gialdi, F. et al. "2-Benziltiobenzamidi Ad Attivitd Antifungina" *II Farmaco—Ed. Sci.* vol. XV, pp. 856-882 (Dec. 6, 1960).

T.W. Greene et al.: "Protective Groups in Organic Synthesis, 3rd Edition, Chapter 6" John Wiley & Sons Inc (2002) pp. 454-457, 460-462, 487-488.

Hinman L M et al: "Preparation and Characterization of Monoclonal Antibody Conjugates of the Calicheamicins: A Novel and Potent Family of Antitumor Antibiotics" *Cancer Research* (Jul. 15, 1993) vol. 53, pp. 3336-3342.

Ibrahim, Y. et al. "Synthesis of Some New Nitrogenous Derivatives of Glycyrrhetic Acid With Potential Biological Activity" *Pak. J. Sci. Ind. Res.* vol. 38 (1995) pp. 101-107.

Koenig, W. et al. "Neue-S-Schutzgruppen Mr Cystein" Chem. Ber. (1968) vol. 101, pp. 681-693.

Ichitoma Miwa et al: "Inhibition of Advanced Protein Glycation by 8-Quinolinecarboxylic Hydrazide" *Pharmacology* (1996) Vopl 52, pp. 314-320.

Nishiyama, Y. et al. "Amino Acids and Peptides. XXVI. Synthesis of Agaricus bisporus Metallothionein and Related Peptides and Examination of Their Heavy Metal-Binding Properties 1'2" Chem. Pharm. Bull. (1990) vol. 38, pp. 2112-2117.

Ohta, N. et al. "Amino Acids and Peptides, VI11.1'2) Synthesis of a Hexacosapeptide corresponding to the C-Terminal Sequence 36-61 of Human Metallothionein II (hMT II) and Determination of its Heavy Metal Binding Activity" *Chem. Pharm. Bull.* vol. 31 (1983) pp. 1885-1895.

Ohta, N. et al. "Amino Acids and Peptides. IX 1,2. Synthesis of Cysteine-Containing Peptide Fragments Related to Human Hepatic Metallothionein II (hMT II) and Determination of Their Heavy Metal-Binding Properties" *Chem. Pharm. Bull.* vol. 31 (1983) pp. 3094-3103.

Okada, Y. et al. "Amino Acids and Peptides. XXIV. Synthesis of Neurospora crassa Metallothionein and Related Cysteine-Containing Peptides and Examination of Their Heavy Metal-Binding Properties 1,2" Chem. Pharm. Bull. (1989) vol. 37, pp. 2322-2329.

Pyzhov, V. K., et al. "Synthesis of Some Esters and Amides of 2-Substituted 4,6-Bis (p-Carboxyphenoxy)-sym-Triazine" CHCCAL, Chem. Heterocycl. Compd. (Engl. Transl. Abstract), (1981) vol. 17, pp. 1057-1062.

Rahman S. et al. "Improved Procedure for Attachment of Amino Acids to Polymer in Peptide Synthesis by Liquid-Phase Method" *Indian Journal of Chem.* vol. 26B (Oct. 1987) pp. 987-988.

Shimoji, Y. et al. "Synthesis and Biological Action of the Aminotetrahydroisoquinocarbazoles and Related Compounds: A New Class of Compounds with Antiarrhythmic Activity" *J. Med. Chem.* vol. 35 (1992) pp. 816-822.

\* cited by examiner

PROCESSES FOR MAKING HYDRAZIDES

CROSS-REFERENCE TO RELATED APPLICATION

Priority is claimed to U.S. patent application Ser. No. 13/755,886, filed on Jan. 31, 2013, now U.S. Pat. No. 8,853,451, which itself claims priority to U.S. patent application Ser. No. 13/360,220, filed on Jan. 27, 2012, now U.S. Pat. No. 8,383,857, which itself claims priority to U.S. patent application Ser. No. 12/123,777, filed on May 20, 2008, now U.S. Pat. No. 8,110,705, which itself claims priority to U.S. Prov. Patent Appl. No. 60/939,529, filed May 22, 2007, all of which are hereby incorporated herein in entirety.

FIELD OF INVENTION

The present invention relates to an improved synthetic method for preparing hydrazides from hydrazine and acyl chlorides. The hydrazide products have a protected thiol group which is used to link calicheamicin to monoclonal antibodies.

BACKGROUND OF THE INVENTION

MYLOTARG® (gemtuzumab ozogamicin), also referred to as CMA-676 or just CMA, consists of a monoclonal antibody against CD33 that is bound to calicheamicin by means of an acid-hydrolyzable linker. When the derivatized calicheamicin binds to the DNA minor groove, it disrupts DNA progression and eventually causes cancer cell death. The commercial product was marketed as the first antibody-targeted chemotherapeutic agent under the name MYLOTARG® and is currently approved for the treatment of acute myeloid leukemia (AML) in elderly patients.

3-Methyl-3-mercaptobutanoic acid hydrazide, also called DMH linker, or CL-332258, is used to link calicheamicin to monoclonal antibodies. The derivatized calicheamicin is then activated for conjugation with a humanized monoclonal antibody to give CMA-676. Currently, DMH linker is prepared through a 5-step reaction process via the intermediate, p-methoxybenzylthioether hydrazide, 5. (Equations I-V). In the present manufacturing process, a Michael addition of p-methoxy-benzylthiol to 3,3 dimethylacrylic acid is assisted by piperidine, (Equation I).

Equation I

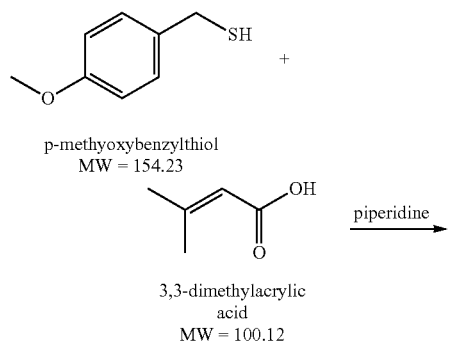

p-methyoxybenzylthiol
MW = 154.23

+

3,3-dimethylacrylic acid
MW = 100.12 piperidine →

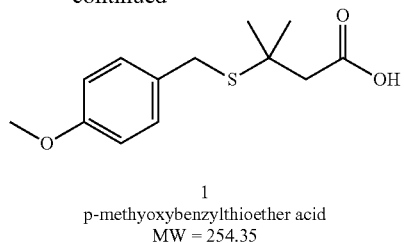

1
p-methyoxybenzylthioether acid
MW = 254.35

The resulting thioether acid (1) reacts with oxalyl chloride in methylene chloride to form p-methoxybenzylthioether acid chloride (2) (Equation II).

Equation II

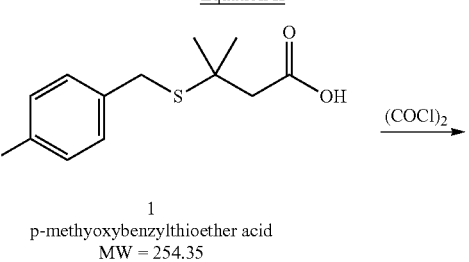

1
p-methyoxybenzylthioether acid
MW = 254.35

(COCl)$_2$ →

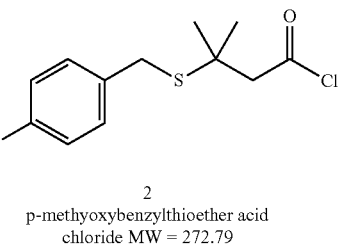

2
p-methyoxybenzylthioether acid
chloride MW = 272.79

Acid chloride (2) is slowly added to a mixture of hydrazine/methylene chloride (in a ratio of about 28%, v/v) at low temperature (−70° C.). The corresponding p-methoxybenzylthioether hydrazide (3) forms in about 74% yield (Equation III):

Equation III

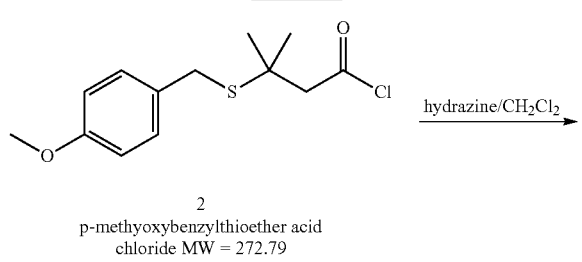

2
p-methyoxybenzylthioether acid
chloride MW = 272.79 hydrazine/CH$_2$Cl$_2$ →

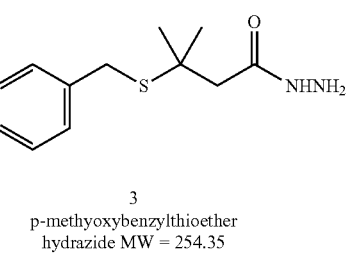

3
p-methyoxybenzylthioether
hydrazide MW = 254.35

However, the desired product p-methoxybenzylthioether hydrazide (3) typically contains about 20% of an undesired by-product, bis-methoxybenzylthioether hydrazide (see Equation VI below). Removing the benzyl protecting group under acidic conditions (Equation (IV), followed by neutralization of the acid salt and purification (Equation V) provides 3-methyl-3-mercaptobutanoic acid hydrazide (5) in 45% yield.

Equation IV

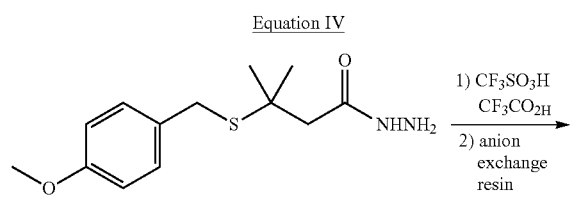

3
p-methyoxybenzylthioether
hydrazide MW = 268.38

4
MW = 184.69

Equation V

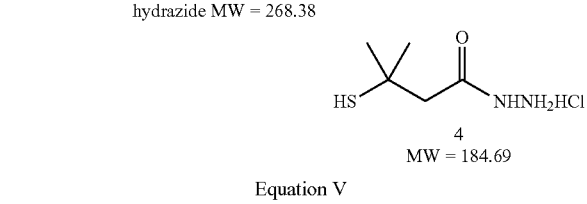

4
MW = 184.69

5
MW = 148.23

An undesired by-product, bis-methoxybenzylthioether hydrazide (6) is generated from the reaction of the product p-methoxybenzylthioether hydrazide with the starting material p-methoxybenzylthioether acid chloride (Equation VI). The generation of this by-product results in lower yield and quality.

Equation VI

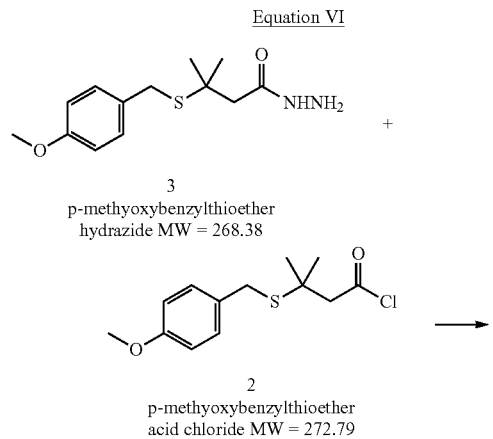

3
p-methyoxybenzylthioether
hydrazide MW = 268.38

2
p-methyoxybenzylthioether
acid chloride MW = 272.79

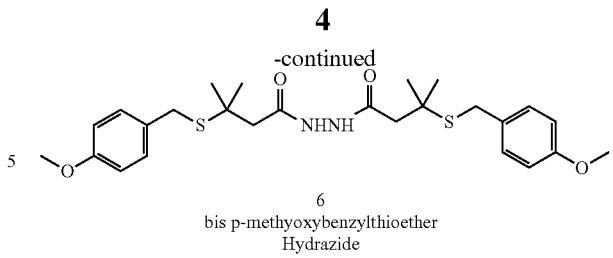

6
bis p-methyoxybenzylthioether
Hydrazide

Using original process procedures, the bis-methoxybenzylthioether hydrazide (6), is generated in amounts of about 20%. The presence of this level or greater of undesired by-product from Equation III is clearly undesirable. The present invention describes techniques which overcome this problem and decrease the yield of the undesired by-product.

SUMMARY OF THE INVENTION

Figure 1:
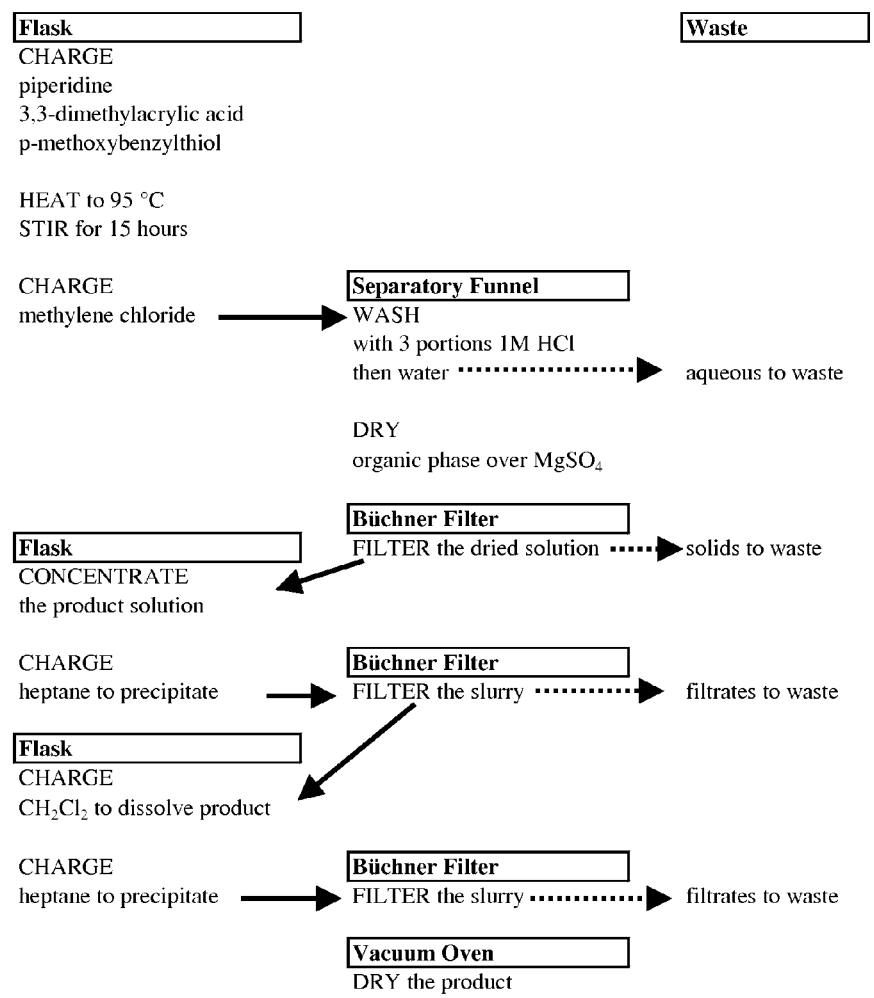
FIG. 1 is a process schematic for preparing p-Methoxybenzylthioether Acid (1).
Figure 2:
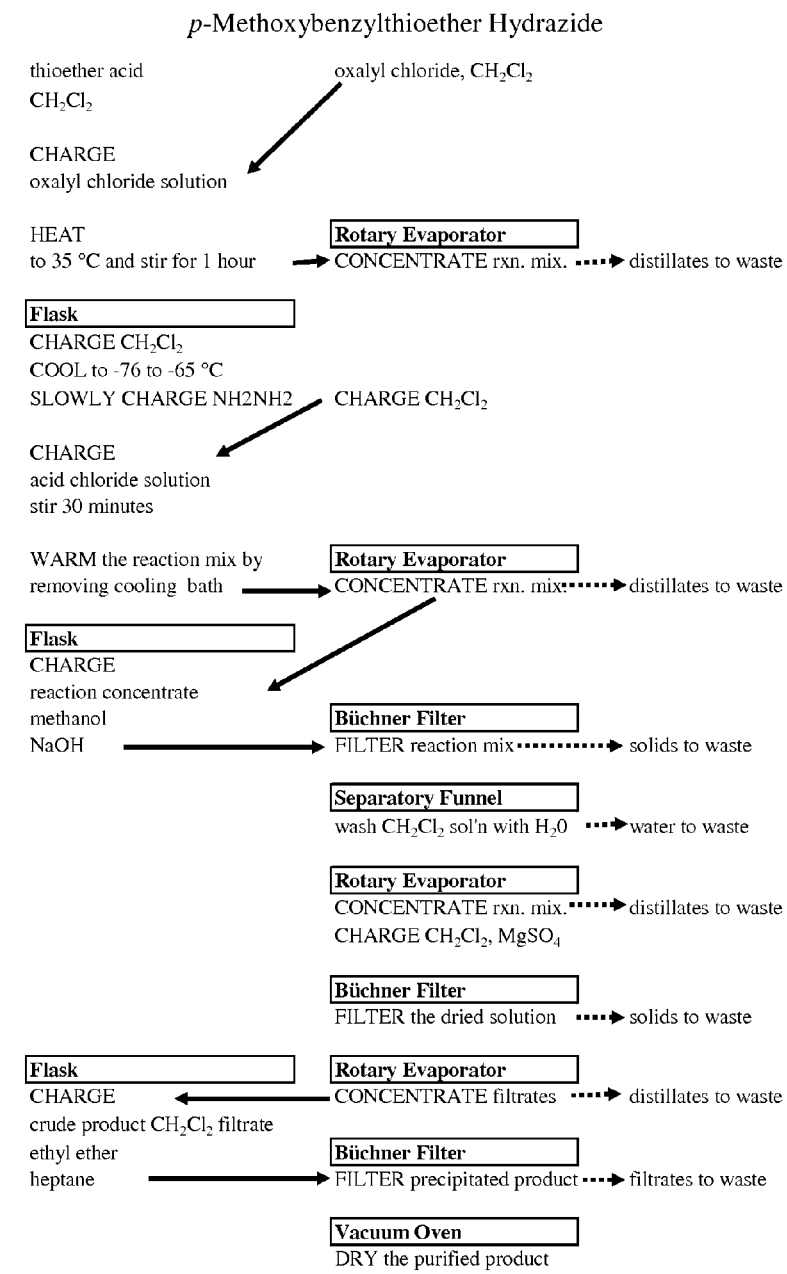
FIG. 2 is a process schematic for preparing p-Methoxybenzylthioether Acid Chloride (2) and p-Methoxybenzylthioether Acid Hydrazide (3).
Figure 3:
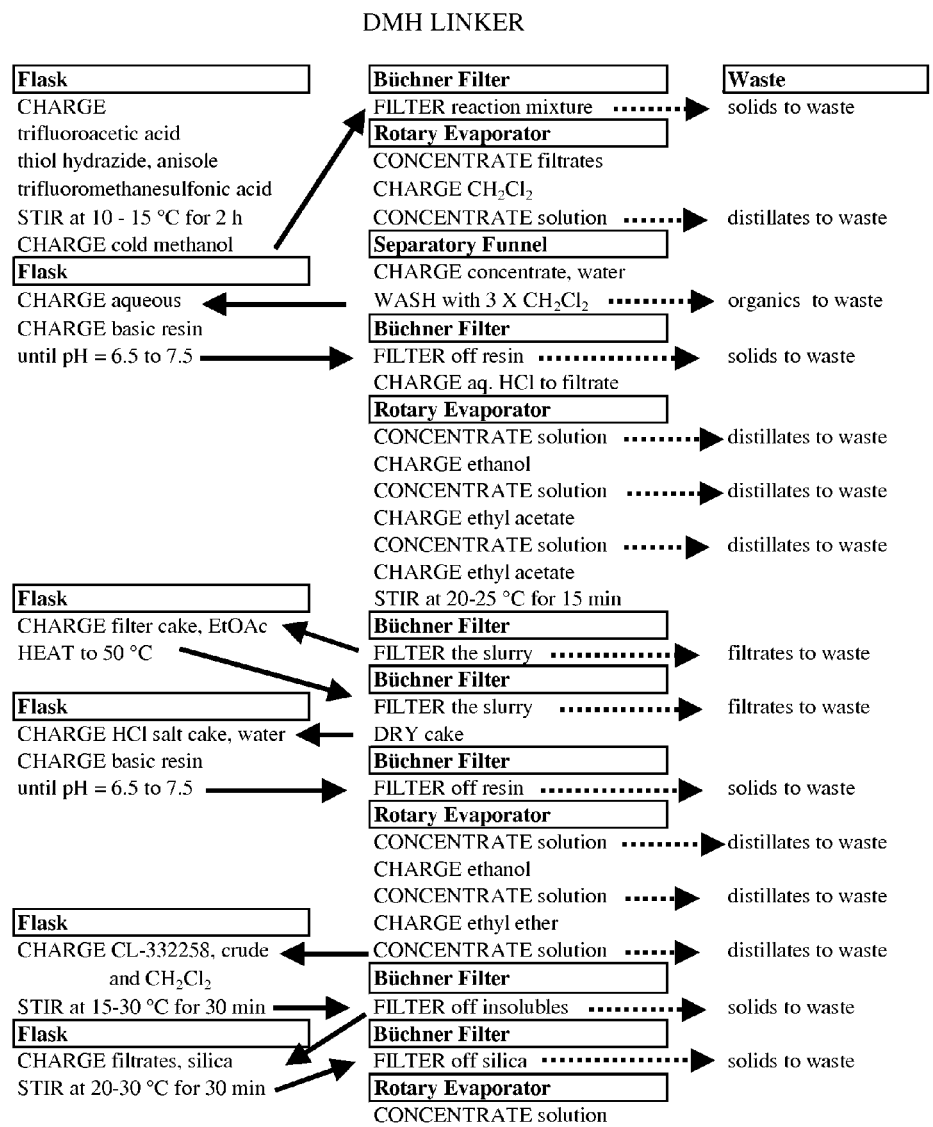
FIG. 3 is a process schematic for preparing DMH LINKER (5).

Certain embodiments of the present invention provide processes for synthesizing hydrazides (e.g., 3-methyl-3-mercaptobutanoic acid hydrazide (4)) while reducing the level of the by-product bis-methoxybenzylthioether hydrazide (e.g., (6)) from about 20% to about 3 to 5%. In an embodiment of the invention, a methoxybenzylthioether acid chloride (2) solution is added to a stirred hydrazine/methylene chloride mixture which is more dilute than that of the original process (e.g., volume ratio=14% vs. about 24% to 32% v/v in the original process). A preferred volume ratio for dilution is about 14% v/v. Optionally and without limitation other non-reactive (or inert) halogenated solvents instead of or in combination with methylene chloride may be used in the embodiments of the invention described herein to form the hydrazine mixture to which the acid chloride is added. Preferred examples of such other solvents include carbon tetrachloride, chloroform, ethylene dichloride and chlorobenzene. In certain embodiments, the amount of methylene chloride (or corresponding inert solvent) is doubled, significantly reducing the amount of unwanted bis-hydrazide by-product. In certain embodiments, the methoxybenzylthioether acid chloride solution is added to the hydrazine/methylene chloride slurry continuously, at a steady rate, rather than portion wise. In certain embodiments, the addition rate is adjusted to maintain a reaction temperature of −68 to −75° C. In certain embodiments, an agitation speed between 300 to 400 rpm in a round-bottom flask or 270 rpm in a Morton-type flask is used. Certain methods of the invention have afforded p-methoxybenzylthioether hydrazide (3) in 91.1% strength in 85% yield with about 4.7% of the bis-methoxybenzylthioether hydrazide (6) formed.

In another embodiment of the invention, it was found that despite the improvement afforded by using the more dilute methylene chloride system, it was still necessary to scrape frozen crystallized hydrazine off the bottom and sides of the reactor vessel. The standard practice had previously been to cool the methylene chloride/hydrazine solution together to approximately −70° C. This resulted in a significant portion of the hydrazine crystallizing and precipitating on the sides of the vessel. To ensure that all the hydrazine was available for reaction, it was necessary to scrape the material from the walls of the vessel to allow it to form a stirrable slurry. To avoid this situation, an alternative procedure as part of certain embodiments of the present invention was devised. This alternative procedure involves the chilling of the methylene chloride to −68 to −75° C., preferably 70° C., followed by a slow drop wise addition of hydrazine to the cold methylene chloride to form a uniform slurry. This new procedure achieves the formation of a much more uniform hydrazine slurry, which minimizes crystallized hydrazine formation on the inner walls of the flask, and reduces or eliminates the need to scrape the flask. This allows the desired amount of hydrazine to be available for reaction, which helps reduce the formation of the bis-methoxybenzylthioether hydrazide (6).

Certain embodiments of the invention provide a method involving the continuous addition of a methoxybenzylthioether acid chloride (2) solution to a comparatively dilute (from the perspective of the prior process) and stirrable chilled hydrazine/methylene chloride heterogeneous mixture (preferably having a hydrazine concentration of approximately 14%). The methoxybenzylthioether acid chloride solution is added to the hydrazine/methylene chloride slurry continuously, at an approximately steady rate rather than portion wise. The addition rate is preferably adjusted to maintain a reaction temperature of −68 to −75° C. An agitation speed between 300-400 rpm in a round-bottom flask or 270 rpm in a Morton-type flask is preferred. The improved processes of certain embodiments of the invention reduce the level of the by-product, bis-methoxybenzylthioether hydrazide (6), from the previously achieved level of about 20% to about 3 to 5% or lower. The improved synthesis of intermediate 1 improves the efficiency of the overall process of synthesizing MYLO-TARG®.

Certain embodiments of the invention provide a method of preparing a hydrazide from hydrazine and an acyl chloride comprising the steps of (a) preparing a stirred substantially uniform slurry comprising hydrazine and an inert solvent; and (b) adding an acyl chloride continuously to said slurry. In another aspect of this embodiment, the acyl chloride is added substantially drop wise to the slurry in the addition step (b).

Certain embodiments of the invention provide methods of preparing hydrazides from acyl halides and hydrazines. In one embodiment, the preparation is accomplished via a chemical reaction between an electrophilic acyl carbonyl of the acyl chloride and a nucleophilic nitrogen of hydrazine. The particular substituents attached to the acyl carbonyl which are suitable for the invention can be any moiety which does not interfere with hydrazide bond formation, including such moieties which incorporate protecting groups in order to prevent interference with hydrazide bond formation. For example, in certain embodiments of the invention, an acyl halide comprises a protected thiol. Examples of protected thiols include but are not limited to benzyl thioethers.

In another aspect of the invention, acyl chlorides have a structure:

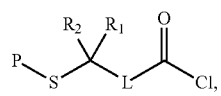

wherein P is a thiol protecting group, $R_1$ and $R_2$ are each selected from the group consisting of $C_1$-$C_5$ alkyl, and L is an alkylene linker. Examples of alkylene linkers L include but are not limited to L is —$(CH_2)_n$—, where n is an integer 1 to 5. In certain embodiments, $R_1$ and $R_2$ are the same, such as when $R_1$ and $R_2$ are both the same $C_1$-$C_5$ alkyl. Examples of $C_1$-$C_5$ alkyl include but are not limited to methyl, ethyl, propyl, butyl, pentyl, including both linear and branched isomers thereof. Examples of thiol protecting groups include but are not limited to a benzyl group, wherein the phenyl moiety is optionally substituted. Examples of optional substituents include but are not limited to an alkoxy, such as methoxy, ethoxy and the like. Accordingly, in one embodiment of the invention, an acyl chloride has the structure:

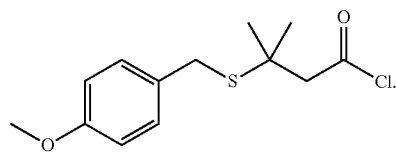 [SMILES: COc1ccc(CSC(C)(C)CC(=O)Cl)cc1]

Another embodiment of the present invention is a method of preparing a hydrazide from hydrazine and an acyl chloride comprising a first step of preparing a stirred substantially uniform slurry comprising hydrazine and an inert solvent. In another aspect of this embodiment, an inert solvent is methylene chloride.

Another embodiment of the present invention is a method of preparing a hydrazide from hydrazine and an acyl chloride. In another aspect of this embodiment, a hydrazide product has the structure:

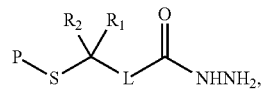

wherein P is a thiol protecting group. In yet another aspect of this embodiment, P is a benzyl group, optionally substituted on the phenyl ring. In another aspect of this embodiment, P is p-methoxybenzyl group and $R_1$ and $R_2$ are each selected from the group consisting of $C_1$-$C_5$ alkyl and L is an alkylene linker. Examples of alkylene linkers include but are not limited to L is —$CH_2$—. In one embodiment, $R_1$ and $R_2$ are each independently methyl.

Another embodiment of the present invention are hydrazide products prepared according to methods of the present invention. In one embodiment, a desired hydrazide has a structure:

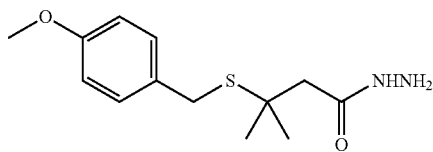 [SMILES: COc1ccc(CSC(C)(C)CC(=O)NN)cc1]

or a salt thereof. In yet another embodiment of the invention, the hydrazide is 3-methyl-3-mercaptobutanoic acid hydrazide.

In another aspect of the invention, the desired hydrazide product contains less than 5% of a bis-hydrazide by-product having the structure:

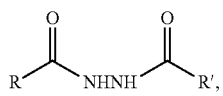

wherein R and R' are optionally substituted alkyl, heteroalkyl, or heteroalkaryl groups.

In another aspect of this embodiment, R and R' moieties in a bis-hydrazide by-product are each

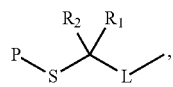

in which P is a thiol protecting group, $R_1$ and $R_2$ are each selected from the group consisting of $C_1$-$C_5$ alkyl, and L is an alkylene linker. Examples of alkylene linkers, L, include but are not limited to —$CH_2$—. In another aspect of this embodiment, $R_1$ and $R_2$ are each independently methyl. In another aspect of this embodiment, P is a benzyl group, optionally substituted on the phenyl ring; examples include but are not limited to P is p-methoxybenzyl group.

Another embodiment of the invention is a method of preparing a hydrazide from hydrazine and an acyl chloride wherein the hydrazide product contains less than 5% of a bis-hydrazide by-product having a structure:

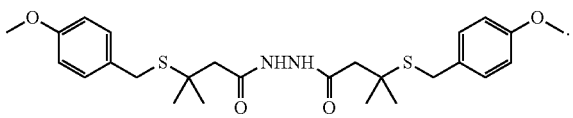

Another embodiment of the present invention is a method of preparing a hydrazide from hydrazine and an acyl chloride comprising a first step of preparing a stirred substantially uniform slurry comprising hydrazine and an inert solvent, and second step of then adding an acyl chloride continuously to the slurry. In another aspect of this embodiment, the continuous addition of acid chloride solution is adjusted to maintain reaction temperature of about −68° C. to about −75° C. In yet another aspect of this embodiment, the hydrazine slurry is substantially uniform.

In another embodiment of the invention, a hydrazide linkage is prepared according to a method comprising the steps of (a) cooling a reaction vessel comprising a stirred inert solvent to a desired low temperature; (b) adding hydrazine in a continuous fashion to said reaction vessel thereby preparing a stirred substantially uniform slurry comprising the hydrazine and the inert solvent; (c) adding an acid chloride to said slurry in a continuous fashion, thereby forming a hydrazide linkage. In another aspect of this embodiment, the inert solvent is methylene chloride.

In another embodiment of the invention, a hydrazine slurry is prepared by a method comprising the steps of (a) chilling an inert solvent to a temperature of about −68° C. to about −75° C., and (b) adding hydrazine dissolved in an inert solvent drop wise to the cold inert solvent. In another aspect of this embodiment, the inert solvent is methylene chloride. In still another aspect of this embodiment, the hydrazine slurry is stirred at a speed of about 270 to about 400 rpm.

Another embodiment of the invention is a method of preparing gemtuzumab ozogamicin comprising the steps of preparing the linker 3-methyl-3-mercaptobutanoic acid hydrazide and using said linker to link calicheamicin to the monoclonal antibody gemtuzumab.

DETAILED DESCRIPTION OF THE INVENTION p-Methoxybenzylthiol undergoes a Michael addition with 3,3-dimethylacrylic acid in piperidine. The quantities of reagents affect the outcome of the reaction. In one embodiment, the quantity of p-methoxybenzyl thiol is in slight molar excess over the 3,3-dimethylacrylic acid, such as the range of between 0.354 (2.3 mol) and 0.362 kg (2.35 mol). If the amount is below this range, the subsequent reaction may be incomplete. If the amount is above this range, the excess reagent may complicate processing. The reaction mixture is heated, taking care not to exceed about 98° C. for a minimum of about 15 hours in order to avoid the excessive formation of impurities. The piperidine is removed by dilution with methylene chloride and washing with aqueous hydrochloric acid and then water. Keeping the temperature above 50° C. and less than 90° C. is necessary before and during the addition of HCl to avoid precipitating the reaction product. The reaction is further cooled and then extracted with methylene chloride as directed in the experimental section.

The amounts of solvents used are proportional to the scale of the reaction for optimum results and purification. The resulting $CH_2Cl_2$ product solution is dried with magnesium sulfate, clarified, concentrated under vacuum, then diluted with heptane to precipitate the crude intermediate, which is filtered and washed with heptane. Purification is accomplished by redissolving the crude material in methylene chloride and precipitating again with heptane. The purified p-methoxybenzylthioether acid (1) is isolated by filtration, washed with heptane and dried under vacuum.

p-Methoxybenzylthioether acid (1) is converted to the corresponding acid chloride using oxalyl chloride with methylene chloride as the solvent. Oxalyl chloride should be present in molar excess with respect to the p-methoxybenzylthioether acid for complete reaction. Acid chloride product is isolated by concentration under vacuum to remove methylene chloride/excess oxalyl chloride to an oil. The resulting oil is diluted with methylene chloride and added slowly over time for about 3 to 5 hours at a temperature range of 65 to 75° C. to a diluted mixture of hydrazine and methylene chloride.

One aspect of the present invention is the formation of a uniform slurry comprising hydrazine and an inert solvent such as methylene chloride. According to one embodiment of the invention, a uniform slurry is prepared by the slow drop wise addition of liquid hydrazine to methylene chloride which had been pre-chilled to about 68 to −75° C., preferably −70° C., prior to commencing the addition of hydrazine. By contrast, cooling a premixed solution of hydrazine in methylene chloride to the same temperature results in the less favorable formation of a crystalline hydrazine which collects on the sides of the reaction vessel. Without being bound to theory, it is believed that the slow, drop wise addition of hydrazine to the pre-chilled methylene chloride and control of the maximum concentration of hydrazine in the methylene chloride results in the formation of smaller, more uniform crystals of hydrazine which remain suspended in the stirred mixture of methylene chloride and substantially do not freeze to the walls of the vessel. Formation of a substantially uniform slurry helps to ensure that hydrazine remains in contact with the stirred methylene chloride and is available for reaction with the incoming acid chloride solution. Formation of a uniform slurry obviates the need to scrape the inside of the reaction flask as required in the prior process. Additionally, this ensures that the desired amount of hydrazine is available for reaction, which also reduces the amount of bis-methoxybenzylthioether hydrazide (6) formed.

The concentration of hydrazine in methylene chloride affects the amount of bis-methoxybenzylthioether hydrazide (6) that is formed as a by-product. In prior processes, the concentration of hydrazine/methylene chloride was about 24 to 32% v/v. Halving the ratio of hydrazine/methylene chloride (more dilute hydrazine) to about 12 to 16% v/v, preferably about 14% v/v, resulted in a decrease in the amount of undesired bis-methoxybenzylthioether hydrazide (6) formed (see Table 1).

TABLE 1

PROCESS RESULTS AFTER IMPROVEMENT

| Exp. No. | Strength of hydrazide* (%) | Bis-hydrazide by-product (%) | Corrected Hydrazide Yield (%) |
|---|---|---|---|
| 1.1 | 91.61 | 9.69 | 85.4 |
| 1.2 | 95.08 | 5.76 | 87.7 |
| 1.3 | 96.16 | 4.13 | 89.6 |
| 1.4 | 93.76 | 7.36 | 85.7 |

*as determined by high pressure liquid chromatography

In certain embodiments of the invention, the acid chloride solution is added to the hydrazine/methylene chloride slurry continuously, at a steady rate rather than portion wise. The amount of added acid chloride and rate of its addition both affect the yield of desired methoxybenzylthioether (3). If too little acid chloride is added, excessive amounts of bis-methoxybenzylthioether hydrazide (6) by-product may form. Also, if the addition time of acid chloride is too short, less than the 3 hrs, excessive amounts of bis-methoxybenzylthioether hydrazide (6) by-product may form. The addition rate is adjusted to maintain a reaction temperature of −68 to −75° C. If the reaction temperature rises to higher temperatures, excessive amounts of the bis-methoxybenzylthioether hydrazide (6) may also form. An agitation speed between 300 to 400 rpm in a round-bottom flask or 270 rpm in a Morton-type flask is preferably used to stir the hydrazine slush. Both aspects of the improved process, use of a more dilute hydrazine/methylene chloride mixture and the formation of a uniform slurry, reduce the level of the by-product, bis-methoxybenzylthioether hydrazide (6), from about 20% to about 3 to 5%. The improved process steps of forming the hydrazine improves the overall efficiency of synthesizing the linker 3-methyl-3-mercaptobutanoic acid hydrazide and therefore also improves the overall efficiency of preparing MYLOTARG® (gemtuzumab ozogamicin).

Upon reaction completion, the reaction mixture is concentrated under vacuum and the residue is treated with methanolic sodium hydroxide (about 4 to 5%). This solution is concentrated under vacuum, diluted with methylene chloride, washed with water, dried over magnesium sulfate, clarified, and concentrated under vacuum to a concentrate. Care should be taken to use sufficient magnesium sulfate to completely dry the product so there is no decomposition or interference with crystallization of the product in the next synthetic step. The final concentrate is diluted with methylene chloride in an amount of 1.33 times the weight of p-methoxybenzylthioether acid (1), and this solution is added to diethyl ether in an amount of 7.6 times the weight of p-methoxybenzylthioether acid (1). An aliphatic hydrocarbon solvent such as heptane, hexane, octane or iso-hexane, preferably heptane, in an amount of 1.83 times the weight of p-methoxybenzylthioether acid (1) is added to the resulting slurry to complete the precipitation. The p-methoxybenzylthioether hydrazide (6) is isolated by filtration, washed with heptane, and dried under vacuum.

p-Methoxybenzylthioether hydrazide (3) is treated with trifluoromethanesulfonic acid in the presence of anisole, using trifluoroacetic acid as a solvent. Care must be taken during the addition and subsequent reaction time not to exceed a reaction temperature of about 20° C. in order to avoid the formation of undesired impurities. After cleavage of the p-methoxybenzyl protecting group is complete, the reaction mixture is quenched into methanol and filtered to remove solid by-products. The filtrates are concentrated under vacuum, dissolved in water, washed with methylene chloride, and treated with an anionic exchange resin to give 3-methyl-3-mercaptobutanoic acid hydrazide (5). The resin is removed by filtration and then aqueous hydrochloric acid is added to the crude product solution to form the HCl salt. The batch is concentrated under vacuum, dissolved in ethanol, clarified by filtration, and concentrated under vacuum. This concentrate is diluted with ethyl acetate and concentrated under vacuum. Again, the residue is diluted with ethyl acetate then isolated by filtration. The wet cake is heated with ethyl acetate to about 48 to 55° C., cooled, filtered, and suction dried. The dried HCl salt is converted to the free base by treatment with an anionic exchange resin in water. The resin is removed by filtration and the filtrates are concentrated under vacuum. The concentrate is dissolved in ethanol, concentrated under vacuum, slurried in diethyl ether, and concentrated under vacuum. As a final purification, 3-methyl-3-mercaptobutanoic acid hydrazide (5) is dissolved in methylene chloride, clarified by filtration, and treated with silica, which is then removed by filtration. The purified product in solution is isolated by concentration under vacuum. In a preferred purification method, demonstrated in Example 15, 3-methyl-3-mercaptobutanoic acid hydrazide (5) is dissolved in 50 parts (v/w) of methylene chloride at 20° C.±3° C., stirred 30 minutes and filtered. The resulting solution is treated with 0.7-1 part (w/w vs crude linker) silica gel, stirred 30 minutes, filtered, and concentrated to dryness on a rotary evaporator. The resulting solid is triturated with n-heptane. After isolation and drying in vacuo, 3-methyl-3-mercaptobutanoic acid hydrazide (5) is obtained as a free flowing solid in approximately a 76% yield.

One aspect of the present invention is a process that provides p-methoxybenzylthioether hydrazide with less than 5% of the undesired by-product, bis-methoxybenzylthioether hydrazide (6). This improved process comprises a modified method for the coupling of thioether acid chloride with hydrazine to form p-methoxybenzylthioether hydrazide. The process steps are shown schematically in Equation I. The undesired by-product, bis-methoxybenzylthioether hydrazide (6), is generated from the coupling of the product, p-methoxybenzylthioether hydrazide (3), with the starting material, p-methoxybenzylthioether acid chloride (2). The generation of undesired bis-methoxybenzylthiothioether hydrazide (6) results in lower quality and yield.

In another aspect of the present invention, the process disclosure may be conceptually understood to encompass broader applications. The specific reaction sequence (Equation III) may be generalized in terms of Equation VII:

Equation VII

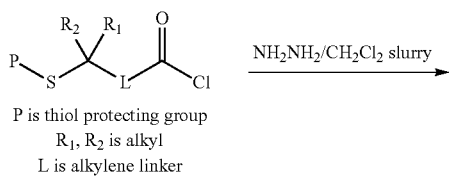

P is thiol protecting group
$R_1, R_2$ is alkyl
L is alkylene linker

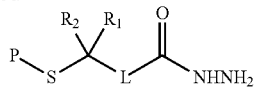

Where a material is described as added continuously in a process step, such addition is meant to occur steadily for a period of time rather than portion wise or all at once. Drop wise addition of a liquid or addition of a liquid through a steady stream are examples of continuous addition. In certain embodiments, continuous addition is accomplished by controlling the rate of addition of a material which reacts exothermally at a rate slow enough to maintain a reactant temperature within a certain temperature range.

Slurry as used herein refers to a combination of solid and liquid phases that are intimately mixed together and typically chilled to a temperature which supports the presence of both solid and liquid phases whereas the mixture would be purely liquid at ambient temperatures. Slurry is sometimes used to refer to a mixture of a solid/liquid mixture of the same substance such as an ice/water mixture in which the ice is relatively finely divided and intimately mixed with the liquid water. In the context of this invention, slurry can refer to a solid/liquid mixture formed from the combination of two materials such as hydrazine and a solvent such as methylene chloride. In a chilled hydrazine/methylene chloride slurry, the liquid phase is believed to contain a mixture of methylene chloride and hydrazine while the solid phase is believed to primarily be hydrazine.

The term "alkyl" includes a straight or branched alkyl having 1 to 10 carbon atoms and a lower alkyl having 1 to 5 carbon atoms is preferable. For example, methyl, ethyl, n-propyl, isopropyl, n-butyl, isobutyl, sec-butyl, tert-butyl, n-pentyl, isopentyl, neopentyl, tert-pentyl, 2-methylbutyl, n-hexyl, isohexyl, heptyl, isoheptyl, octyl, isooctyl, nonyl, decyl and the like are included. The term "alkylene" includes straight and branched diradicals of alkanes having one to 10 carbons such as methylene (—$CH_2$—), ethylene (—$CH_2CH_2$—), propylene, butylene, and pentylene.

The term "heteroalkyl" refers to an alkyl group as defined herein where one or more carbon atoms are replaced by a heteroatom (an oxygen, sulfur, nitrogen, or phosphorus atom) and may optionally contain additional heteroatoms. The term heteroalkaryl refers to a heteroalkyl moiety as described above but which is further substituted with an aryl moiety wherein such aryl moiety may be optionally substituted. Optionally substituted aryl includes phenyl and substituted phenyl. In substituted phenyl, one, two or three optional substituents may substitute for hydrogen on a phenyl ring and be situated ortho, meta, and/or para to the methylene group of the benzyl carbon (or other point of attachment). In Example 1, a methoxy group is situated para to the methylene group. Non-limiting examples of optional aryl substituents include, $C_1$-$C_5$ alkyl, $C_1$-$C_5$ alkoxy, $C_1$-$C_5$ haloalkyl, $C_1$-$C_5$ haloalkoxy, wherein the hydrogen atoms attached to the alkyl or alkoxy carbons may be replaced by halogen atoms, as for example, in —$CF_3$ and —$OCF_3$.

The following non-limiting examples illustrate the invention.

Example 1

Original Preparation of p-Methoxybenzylthioether Acid (1)

With reference to Equation I, a 5-L round bottomed flask, equipped with a thermocouple, mechanical stirrer, reflux condenser topped with $N_2$ inlet, and 250 mL pressure equalizing addition funnel, was charged with 400 g, 465 mL, 4.70 mol of piperidine. 3,3-dimethylacrylic acid (215 g, 2.15 mol) was added portion wise into a stirred 5-L reaction flask. The reaction was vigorously stirred under $N_2$. The reaction temperature was maintained to less than 35 to 40° C. during the addition (Note: strong exotherm, i.e., off gassing). p-Methoxybenzylthiol (386 g, 323 mL, 2.32 mol) was charged via pressure equalizing addition funnel over 15 minutes into the (5-L) reaction flask. The mixture was heated to 82 to 88° C., with stirring under $N_2$. The reaction temperature was maintained in this range for 15 minutes. Note: exothermic. The clear yellow mixture was heated to 92 to 95° C. with stirring under $N_2$ for a minimum of 15 hours. A 1 mL sample was removed for HPLC analysis. The reaction was deemed complete when less than 3% by area of the 3,3-dimethylacrylic acid remained. The reaction was cooled to 70 to 75° C. by removing the heating mantle.

3M hydrochloric acid solution (1,900 mL, 2,090 g) was added via a 1-L pressure equalizing addition funnel to the stirred yellow solution while maintaining the temperature to less than 90° C. The final temperature was 70 to 75° C. The mixture was cooled to 20 to 25° C. by applying a cool water bath. Methylene chloride (1,600 g, 1,210 mL) was charged to the heterogeneous mixture. The mixture was stirred for 5 minutes. The pH of the upper aqueous layer in the flask was checked and 3M HCL was added as necessary until the aqueous layer had pH less than 2. The entire contents of the 5-L reaction flask was transferred to a 4-L separatory funnel. The two layers were allowed to separate for a minimum of 10 minutes. The organic (bottom) layer was transferred from the separatory funnel back into the 5-L reaction flask. The aqueous (top) layer was transferred from the separatory funnel into a (4-L) Erlenmeyer flask. 3M hydrochloric acid solution (1,050 mL, 1,154 g) was charged via 1,000 mL pressure equalizing addition funnel to the methylene chloride solution in the 5-L vessel over 10 minutes. The pH of the upper aqueous layer in the flask was checked and 3M HCL was added as necessary until the aqueous layer pH was less than 2. The entire contents of the 5-L reaction flask was transferred to a 4-L separatory funnel. The combined volume was recorded. The two layers were allowed to separate for a minimum of 10 minutes. The organic (bottom) layer was transferred from the separatory funnel into a clean 4-L Erlenmeyer flask. The aqueous (top) layer was transferred from the separatory funnel into a clean 4-L Erlenmeyer flask. The aqueous layers were combined into a 5-L reaction flask.

Methylene chloride (305 mL, 400 g) was charged into the aqueous solution obtained in the previous step. The mixture was stirred for a minimum of 5 minutes. The entire contents of the 5-L flask was transferred to a 6-L separatory funnel and the combined volume was recorded. The two layers were allowed to settle for at least 5 minutes. The organic (bottom) layer was transferred from the separatory funnel into the 4-L Erlenmeyer flask. The methylene chloride solution was washed with 1,000 mL of water. The mixture was stirred thoroughly for 1 to 2 minutes and then allowed to settle for a minimum of 10 minutes. The aqueous layer was separated. The pH of the aqueous layer in the flask was measured. The aqueous layers were combined and discarded. Anhydrous magnesium sulfate (110 g) was added to the methylene chloride solution and stirred for at least 15 minutes. A (5-L) reaction flask was pre-marked at 800, 900 and 1,000 mL levels. Using suction, the yellow mixture was filtered through a 15 cm Buchner funnel with filter paper (Whatman #1) into a 5-L reaction flask. The flask and filter cake were rinsed with 300 mL, 400 g of methylene chloride. The methylene chloride solution was concentrated as follows: The 5-L round-bottomed flask was equipped with a mechanical stirrer and a Claisen still head fitted with a thermocouple. The still head was connected to a 30-cm simple condenser, and the condenser was attached to a receiver adaptor which was fitted with a 1-L flask cooled in an ice bath. The receiver adaptor was connected to an ice cold trap. The cold trap was connected to a vacuum pump.

Methylene chloride from the solution in the 5-L flask was distilled at a temperature of 15 to 35° C., under vacuum, until a pot volume of about 900 mL was attained. The distillate was discarded. The temperature of the contents of the 5-L reaction flask was adjusted to from 15 to 20° C. Heptane (2,442 mL, 1,670 g) was charged via a pressure equalizing addition funnel to the stirred concentrate solution over a minimum of about 10 minutes. A precipitate formed after addition of approximately 1,000 ml, 684 g heptane. The heterogeneous mixture was cooled with stirring to a temperature of from 0 to 5° C. over a minimum of 20 minutes and held at that temperature for a minimum of 30 minutes. The contents of the 5-L reaction flask were filtered through a 30 cm Buchner funnel with Whatman #1 filter paper. The filtrate was collected in a 4-L suction flask. The 5-L reaction flask was rinsed to the filter cake with 2×310 mL, 2×212 g of heptane. The filter cake was dried with suction until essentially no more filtrate was collected and for a minimum of 25 minutes. The filter cake height was about 20 mm. The filter cake weight was about 601 g. The filtrate was discarded. The cake was transferred into a 5-L round bottomed flask equipped with thermocouple, a mechanical stirrer, an $N_2$ inlet and a 1-L pressure equalizing addition funnel. Methylene chloride (750 mL, 990 g) was charged into the 5-L reaction flask and stirred until all solids dissolved (about 10 minutes). Heptane (1,060 mL, 725 g) was charged into the 5-L reaction flask. The heterogeneous solution was cooled to 0 to 5° C. using an ice bath over a minimum of 15 minutes and then stirred for at least 30 minutes. A thick heterogeneous solution was observed. The contents of the 5-L reaction flask were filtered on 30 cm Buchner funnel with Whatman #1 filter paper. The filtrate was collected in a 4-L suction flask. The 5-L reaction flask was rinsed to the filter cake with 2×310 mL, 2×212 g heptane. The filter cake was dried with suction until essentially no more filtrate was collected (a minimum of 20 minutes). The filter cake height was about 20 mm. The filter cake weight was about 632 g. The filtrate was discarded. The wet cake was transferred into a drying dish. The drying dish containing the p-methoxybenzylthioether acid was covered with clean filter paper. The product was dried in a vacuum oven at 38 to 40° C. and 28 to 30 inch Hg vacuum for at about 20 hours.

Example 2

Original Preparation of p-Methoxybenzylthioether Acid Chloride (2)

With reference to Equation II, p-Methoxybenzylthioether acid (400 g, 1.57 mol) was charged into a 5-L round bottomed flask equipped with a thermocouple, a mechanical stirrer, a reflux condenser topped with $N_2$ inlet, and a 0.5-L pressure equalizing addition funnel. Methylene chloride (1,600 g, 1,212 mL) was charged into the 5-L reaction flask. The clear solution was heated to 20 to 25° C. Methylene chloride (300 g) and oxalyl chloride (110 g, 78 mL) were charged into the 0.5-L pressure equalizing addition funnel. 350 mL of oxalyl chloride/methylene chloride solution were added via the addition funnel while maintaining the reaction temperature at 20 to 30° C. The clear yellow solution was stirred at 20 to 25° C. for a minimum of 30 minutes until bubbling subsided. Addition of oxalyl chloride was repeated. 350 ml of oxalyl chloride/methylene chloride solution were added via the pressure equalizing addition funnel to the reaction flask while maintaining reaction temperature at 20 to 30° C. (Addition time about 45 minutes). The reaction mixture was heated to about 32 to 38° C. The stirred solution was held in this temperature range for a minimum of 1 hour. A 1 mL sample was removed for HPLC analysis. The reaction was deemed complete when less than 3% by area of the methoxybenzylthioether acid starting material remained. The reaction was cooled to from 23 to 28° C. over a minimum of 5 minutes. The solution was transferred to a tared 3-L round bottom flask. The reaction flask was rinsed to the 3-L flask with 100 ml, 132 g methylene chloride. The reaction solution was concentrated solution in vacuo, by rotary evaporator with bath temperature set at 33 to 36° C. and a pressure of 25 to 28 inch Hg, until no volatiles remained. The final weight was 1,367 g and the net weight was 500.3 g of p-methoxybenzylthioether acid chloride. Distillate was discarded.

Example 3

Original Preparation of p-Methoxybenzylthioether Hydrazide (3)

With reference to Equation III, a 5-L Morton type round bottomed flask was equipped with a thermocouple, a mechanical stirrer, a reflux condenser topped with $N_2$ inlet, and a 0.5-L pressure equalizing addition funnel. p-methoxylbenzylthioether acid chloride was dissolved in 500 ml, 660 g of methylene chloride. The solution was transferred into a 2-L Erlenmeyer flask. 500 ml methylene chloride were added to make up a total volume of 1,300 mL solution.

In a 5-L Morton-type round-bottomed flask (RBF), Morton Type, were charged 2,400 g, 1,818 mL of methylene chloride and 256 g, 245 mL, @ 98% strength, 7.8 mol of anhydrous hydrazine. The mechanical stirrer speed was set at 255-270 rpm. The cloudy slurry was cooled to −69 to −72° C. using dry ice/acetone.

The acid chloride solution was added drop wise to the 5-L reaction flask via the 0.5-L pressure equalizing addition funnel, maintaining a reaction temperature of −68 to −72° C. It was important to adjust the addition rate of methylbenzylthioether acid chloride solution to the stirred hydrazine/methylene chloride slurry at a rate that ensured a reaction temperature of less than −67° C. Addition was complete after about 3 hours. The stirred reaction was held at −68 to −72° C. for a minimum of 30 min. A 1 mL sample was removed for HPLC analysis. The solution was warmed to room temperature (20 to 30° C.) by removing the ice bath.

The reaction mixture was transferred into a tared 3-L round bottom flask. The reaction solution was concentrated in vacuo by rotary evaporator. The bath temperature was set at 32 to 36° C. and pressure 25 to 28 inch Hg. All volatiles were removed. The final weight was 1,490.7 g and the net weight was 630 g of crude, solid p-methoxylbenzylthioether hydrazide. The distillate was discarded.

Methanol (1,250 g, 1,580 mL) was added to crude p-methoxylbenzylthioether hydrazide solid and the heterogeneous mixture was mixed in a 5-L round-bottom flask at 33 to 36° C. for minimum of 5 minutes until a clear solution was obtained. The crude p-methoxylbenzylthioether hydrazide/methanol solution was transferred into a 5-L reaction flask.

1,312 g of 4% sodium hydroxide/methanol solution were charged into the 5 L reaction flask at 28 to 34° C. over 8 minutes. The clear mixture was stirred at 33 to 36° C. for 20 minutes. A light precipitate formed.

The contents of the 5-L reaction flask were filtered on a 30-cm Buchner funnel with filter paper (Whatman #1). The (5-L) reaction flask was rinsed with 200 mL, 158 g of methanol. The filtrate was transferred into a tared 3-L round bottom flask. The reaction solution was concentrated in vacuo, by rotary evaporator. The bath temperature was set at 36 to 40° C. and pressure 25 to 28 inch Hg. All volatiles were removed. The final weight was 1,484 g and the net weight was 622.7 g of crude p-methoxybenzylthioether hydrazide solid. The distillate was discarded. The solid was dissolved in a 700 g, 530 mL of methylene chloride. The heterogeneous mixture was mixed in the rotary evaporator (no vacuum), at 33 to 36° C. for minimum of 10 minutes until clear solution was obtained.

The solution was concentrated in vacuo by rotary evaporator. The bath temperature was set at 36 to 40° C. with a pressure of 28 to 30 inch Hg. All volatiles were removed. The final weight was 1,494.2 g and the net weight was 632.5 g of crude p-methoxybenzylthioether hydrazide solid. The distillate was discarded. The solid was dissolved with 2,100 mL, 2,772 g of methylene chloride. The heterogeneous mixture was mixed at 20 to 25° C. for a minimum of 5 minutes until a clear solution was obtained. 110 g of anhydrous magnesium sulfate was added to the methylene chloride solution, and the mixture was stirred for 1 hour. Using suction, the yellow mixture was filtered through a 15-cm Buchner funnel with filter paper (Whatman #1) into a 5-L reaction flask. The flask and filter cake were rinsed with 500 mL, 660 g of methylene chloride. The filtrate was transferred into a tared 3-L roundbottom flask. The solution was concentrated in vacuo, by rotary evaporator. The bath temperature was set at 32 to 35° C. with pressure of 20 to 25 inch Hg. All volatiles were removed. The final weight was 1,090 g and the net weight was 643 g of crude p-methoxybenzylthioether hydrazide solid. The distillate was discarded.

The solid was dissolved with 400 mL, 528 g of methylene chloride. The heterogeneous mixture was mixed at 35 to 40° C. for minimum of 5 minutes until a clear yellow solution was obtained. 4,260 mL, 3,040 g of ether was charged to a 12-L round bottomed flask equipped with a thermocouple, a mechanical stirrer, an $N_2$ inlet, and a 2-L pressure equalizing addition funnel. The ether was cooled in the 12-L flask to 0 to −10° C. using brine and ice. The yellow p-methoxybenzylthioether hydrazide/methylene chloride solution (prepared above) was added via pressure equalizing addition funnel to the rapidly stirred 300-400 rpm ether while maintaining the temperature at 0 to −10° C. 1,070 mL, 732 g of heptane was charged. The heterogeneous mixture was stirred at 0 to −5° C. for 20 minutes. The contents of the (12-L) reaction flask were filtered through a 30-cm Buchner funnel with filter paper (Whatman #1). The filtrate was collected in a 4-L suction flask. The 5-L reaction flask was rinsed to the cake with 1,070 mL, 732 g of heptane. The filtrate was discarded. The filter cake was dried with suction for a minimum of 50 minutes until essentially no more filtrate was collected. The filter cake height was 15 mm. Filter cake weight was 429 g. The wet cake was transferred into a drying dish. The drying dish containing the methoxybenzylthioether acid was covered with clean filter paper. The product was dried in a vacuum oven at 38 to 40° C. and 28 to 30 inch Hg vacuum for at least 18 hours.

Results for typical batch reactions using the methods of Examples 1-3 are gathered in Table 2.

TABLE 2

TYPICAL BATCHES BEFORE PROCESS IMPROVEMENTS WERE ADDED

| Batch No | Strength of Hydrazide (%) | Bis-hydrazide by-product (%) | Corrected hydrazide Yield (%) |
| --- | --- | --- | --- |
| 2.1 | 78.5 | 22.1 | 67.8 |
| 2.2 | 78.4 | 19.3 | 74.8 |

Example 4

Modified Preparation of p-Methoxybenzylthioether Hydrazide (3)

In order to reduce the level of the by-product, bis-methoxybenzylthioether hydrazide (6), the reaction parameter(s) that influence the formation of this by-product in the isolated product, p-methoxybenzylthioether hydrazide were investigated. The procedure of Example 3 was repeated. At −78° C. the hydrazine/$CH_2Cl_2$ solution is an unstirrable frozen mixture. Gummy lumps stuck to the reaction flask while the stirring blade was spinning in the air. A solution of thioether acid chloride/$CH_2Cl_2$ was added drop wise to this frozen mixture of hydrazine/$CH_2Cl_2$ (28% v/v), while keeping the temperature at about −72° C. HPLC analysis at the end of the addition (temperature was −72° C.) showed little reaction. This was contrary to the expectation that it is a fast reaction. This could be due to lack of proper mixing in the reaction. The largely unreacted reaction mixture was allowed to warm. When the temperature reached about −50° C., a stirrable heterogeneous mixture developed, followed by a rapid exotherm that pushed the temperature instantly to −28° C. where the reaction color changed from yellow to off-white. This led to the postulation that ineffective mixing could lead to localized reaction that favored the generation of the bis-hydrazide. Warming to room temperature and work-up of the reaction as in Example 3 provided the bis-hydrazide as the major product (82%, HPLC area %). This is much higher than the typical undesired level of 20%. It was concluded that the solution of added thioether acid chloride (2)/$CH_2Cl_2$ did not mix effectively with the frozen lumps of hydrazine.

Example 5

Temperature Effects on the Preparation of p-Methoxybenzylthioether Hydrazide (3)

Example 5 repeated the same reaction of Example 4, but was carried at 0° C., rather than at about −72° C. A solution of thioether acid chloride/$CH_2Cl_2$ was added drop wise to a stirrable, homogenous solution of hydrazine/$CH_2Cl_2$ (28% v/v). In this case, 39% (HPLC area %) of the bis-hydrazide formed. These conditions imply that lower temperature and stirring are factors that affect the formation of undesired by-product. The results of Examples 3.1 and 3.2 are gathered in Table 3.

TABLE 3

PREPARATION OF P-METHOXYBENZYLTHIOETHER
HYDRAZIDE AS A FUNCTION OF TEMPERATURE

| Example No. | Hydrazine (Eq.) | Hydrazine/ $CH_2Cl_2$ (v/v) (%) | Temp (° C.) | Bis-hydrazide (%) | Comments |
|---|---|---|---|---|---|
| 3.1 | 5 | 28 | ~−72 | 82 | Poorly stirred |
| 3.2 | 5 | 28 | ~0 | 39 | Stirred slurry | a. The acid chloride was added to the hydrazine/$CH_2Cl_2$ mixture at rate of 0.25 mL/min.

Example 6

Effect of Hydrazine Concentration on the Preparation of p-Methoxybenzylthioether Hydrazide (3)

The effect of using a lower concentration of hydrazine at low temperature was then examined. The results are gathered in Table 4 below. A stirrable, heterogeneous mixture of hydrazine/$CH_2Cl_2$ at −65 to −72° C. was prepared by diluting the hydrazine/$CH_2Cl_2$ to concentrations of 5% and 19% vs 28% (v/v). Experiments 4.1 and 4.2 in Table 4 carried out at hydrazine/$CH_2Cl_2$ concentrations of 19% and 5%, respectively, provided a stirrable, heterogeneous mixture that was reacted with thioether acid chloride to provide desired product with bis-hydrazide by-product levels of 3% and 5%, respectively. Repeating the same reaction using less hydrazine (Experiment 4.3 in Table 4 using 5 vs 10 mol equivalents) generated only 3% of the bis-hydrazide. The typical amount of hydrazine is 5 mol equivalents versus thioether acid. Doubling the amount of hydrazine to 10 mol equivalents (Table 4: Experiments 4.1 and 4.2) did not significantly affect the level of bis-hydrazide in the final product.

Adding the acid chloride at a faster rate (cf. experiments 4.4 and 4.5 in Table 4, which used 1 vs 0.25 mL/min.) to the dilute hydrazine/$CH_2Cl_2$ heterogeneous mixture (5% and 19%) generated bis-hydrazide at levels of 3% and 9%, respectively. The drastic drop in the level of the bis-hydrazide (from 82% to 3%, cf. experiment 3.1 in Table 3 above and experiment 4.4 in Table 4) could be attributed to one or more of the following factors: Temperature, concentration, amount of hydrazine, addition rate and mixing. The 9% bis-hydrazide generated from Experiment 4.5 in Table 4 could be caused by initial ineffective stirring.

TABLE 4

PREPARATION OF P-METHOXYBENZYLTHIOETHER
HYDRAZIDE UNDER VARIOUS DILUTIONS
OF HYDRAZINE/$CH_2CL_2$

| Exp. No. (5 g Scale) | Hydrazine (Eq.) | Addition rate (mL/min.) | Hydrazine/ $CH_2Cl_2$ (v/v) (%) | Bis-hydrazide (%) | Comments |
|---|---|---|---|---|---|
| 4.1 | 10 | 0.25 | 19 | 4 | Stirred slurry |
| 4.2 | 10 | 0.25 | 5 | 5 | Stirred slurry |
| 4.3 | 5 | 0.25 | 5 | 3 | Stirred slurry |
| 4.4 | 5 | 1.0 | 5 | 3 | Stirred slurry |
| 4.5 | 5 | 1.0 | 19 | 9 | Started as non-stirred slurry |

The reaction temperature during the addition was maintained at −68 to −73° C..

Example 7

Effect of Temperature on the Preparation of p-Methoxybenzylthioether Hydrazide (3)

The effect of temperature on the level of bis-hydrazide in the product was examined in Table 5. In experiments where the thioether acid chloride was added to a stirred mixture of hydrazine/$CH_2Cl_2$ (19% v/v) at −20 and −72° C. (Table 5: Experiment 5.1 and 5.2), bis-hydrazide was generated at levels of 28% and 4%, respectively. Similar results were observed in experiments 5.3 and 5.4 (Table 5). The above results indicate a lower reaction temperature (~−70° C.) is necessary to obtain lower levels (3-5%) of the bis-hydrazide.

TABLE 5

THE EFFECT OF TEMPERATURE ON THE LEVEL OF THE
BIS-HYDRAZIDE FORMED

| Experiments[a] (5 g Scale) | Hydrazine/$CH_2Cl_2$ (v/v) (%) | Temp (° C.) | Bis-hydrazide (%) | Comments |
|---|---|---|---|---|
| 5.1 | 19 | −20 | 28 | stirred slurry |
| 5.2 | 19 | −72 | 4 | stirred slurry |
| 5.3 | 5 | −38 | 16 | stirred slurry |
| 5.4 | 5 | −72 | 3 | stirred slurry |

[a]The above experiments were carried out using 5 eq. of hydrazine.

Example 8

Effect of Hydrazine Concentration on the Preparation of p-Methoxybenzylthioether Hydrazide (3)

Examining the experiments in Table 4 revealed that an addition temperature of around −70° C. and a concentration of hydrazine/$CH_2Cl_2$ at either 19% or 5% (v/v) produced comparable results. This observation was further examined in Table 6. In experiments 6.1, 6.2 and 6.4 in Table 6 where the thioether acid chloride was added to the heterogeneous mixture of hydrazine/$CH_2Cl_2$ at concentrations of 19%, 14% and 10%, the bis-hydrazide was generated at levels of 6%, 13% and 4%, respectively. The reaction volume, flask size and agitation speed were kept constant. The results showed that at 19%, the reaction was comparable to the results at 10% concentration. The hydrazine/$CH_2Cl_2$ concentration of 14% was repeated at 30 g scale (Experiment 6.3 in Table 6) to provide the desired product contaminated with only 3% bis-hydrazide. The higher level of bis-hydrazide in Experiment 6.2 is attributed to initial fast addition of acid chloride that caused the reaction temperature to spike to −57° C. before it was quickly adjusted.

TABLE 6

THE EFFECT OF HYDRAZINE/$CH_2CL_2$ CONCENTRATION ON
THE LEVEL OF THE BIS-HYDRAZIDE FORMED

| Exp No.[a] (Scale) | Hydrazine/ $CH_2Cl_2$ (v/v) (%) | Temp (° C.) | Bis-hydrazide (%) | Comments (Liq. vol/RBF size) |
|---|---|---|---|---|
| 6.1 (5 g) | 19 | −68 to −70 | 6 | 20 mL/100 ml |
| 6.2 (4.2 g) | 14 | −57 to −65 | 13 | (Initial fast add.) 20 mL/100 ml |
| 6.3 (30 g) | 14 | −68 to −71 | 3 | 140 mL/500 mL |

TABLE 6-continued

THE EFFECT OF HYDRAZINE/CH$_2$CL$_2$ CONCENTRATION ON
THE LEVEL OF THE BIS-HYDRAZIDE FORMED

| Exp No.[a] (Scale) | Hydrazine/ CH$_2$Cl$_2$ (v/v) (%) | Temp (° C.) | Bis-hydrazide (%) | Comments (Liq. vol/RBF size) |
|---|---|---|---|---|
| 6.4 (2.9 g) | 10 | −61 to −68 | 4 | 20 mL/100 ml |

[a] the above experiments were carried out using 5 equivalents of hydrazine

Example 9

Effect of Mixing Speed on Preparation of p-Methoxybenzylthioether Hydrazide (3)

The effect of mixing was examined (Table 7). Experiments 7.2 and 7.1 showed that faster mixing (400 rpm vs 200 rpm) produced lesser bis-hydrazide (22% vs 40%). The higher than usual level of bis-hydrazide in both experiments could be caused by ineffective mixing considering the initial liquid level (36 mL) of hydrazine/CH$_2$Cl$_2$ in the 50-mL flask compared to 20 mL liquid in 100-mL flask in Table 8. This means that in addition to the speed of the mixing, the reactor geometry and liquid level must be considered.

TABLE 7

THE EFFECT OF MIXING ON THE LEVEL OF THE
BIS-HYDRAZIDE FORMED

| Experiment (5 g scale) | Hydrazine/ CH$_2$Cl$_2$ (v/v) (%) | Temp (° C.) | Bis-hydrazide (%) | Add rate (mL/min.) | Mixing rate (rpm) |
|---|---|---|---|---|---|
| 7.1 | 19 | −60 | 40 | 1 | 200 |
| 7.1 | 19 | −65 | 22 | 1 | 400 | a. The final liquid volume/reactor size was 72%.

Example 10

Scale-Up Effects on Preparation of p-Methoxybenzylthioether Hydrazide (3)

Preparing p-methoxybenzylthioether hydrazide at either concentration of hydrazine/CH$_2$Cl$_2$ of 19% or 5% (v/v) produced comparable results. While the 19% concentration of hydrazine/CH$_2$Cl$_2$ is usually a stirrable mixture at −70° C., there is a risk that it could become a poorly mixed frozen mixture. If a manufacturing scale batch (400 g) were run at 5% concentration of hydrazine/CH$_2$Cl$_2$, a larger reactor (20-L Morton type) could be required. However, if the process is run at 14% concentration of hydrazine/CH$_2$Cl$_2$, the reaction can be carried out using a glass reactor, 5-L Morton type round-bottomed flask. When the process was run at 14% v/v concentration of hydrazine/CH$_2$Cl$_2$ at 20 g scale (Experiment 8.1 in Table 8) the isolated product, p-methoxybenzylthioether hydrazide, was contaminated with 4.4% (HPLC area %) of by-product, bis-methoxybenzylthioether hydrazide. Repeating the above condition (concentration of hydrazine/CH$_2$Cl$_2$ was 14%) at manufacturing scale-up conditions (Experiment 8.2 in Table 8) produced p-methoxybenzylthioether hydrazide contaminated with 4.2% (HPLC area %) of by-product, bis-methoxybenzylthioether hydrazide.

TABLE 8

PREPARATION OF P-METHOXYBENZYLTHIOETHER
HYDRAZIDE AT HYDRAZINE/CH$_2$CL$_2$ CONCENTRATION
WAS 14%

| Exp. No. (Scale) | Flask size (mL) | Initial Liq. level/ reactor size (%) | Bis-hydrazide HPLC area % (%) |
|---|---|---|---|
| 8.1[a] (20 g) | 250 | 39[c] | 4.4 |
| 8.2[b] (400 g) | 5000 (Morton) | 39[c] | 4.2 |

[a]The concentration of hydrazine/CH$_2$Cl$_2$ mixture is 14% (v/v)
[b]The concentration of hydrazine/CH$_2$Cl$_2$ mixture is 14% (v/v).
[c]The initial volume reactor size = 39%. Final liquid volume/reactor size = 64%.

The original process (Table 9, experiment 9.1), provided the product, p-methoxybenzylthioether hydrazide, in 78.4% strength that contained 19.3% of by-product, bis-hydrazide. The modified process in Experiment 9.2, Table 9, used continuous addition of a methoxybenzylthioether acid chloride solution to a more dilute and stirrable hydrazine/methylene chloride heterogeneous mixture (concentration was 14%). The product, p-methoxybenzylthioether hydrazide, was prepared in 91.1% strength that contained 4.7% of by-product, bis-hydrazide.

TABLE 9

COMPARISON BETWEEN THE MODIFIED PROCESS AND
THE PREVIOUS PROCESS FOR THE PREPARATION OF
P-METHOXYBENZYLTHIOETHER HYDRAZIDE

| Process (Scale) | Mixing speed (RPM) | Flask size (mL) | p-Methoxybenzylthioether hydrazide (Strength %) | Bis-hydrazide (%) |
|---|---|---|---|---|
| 9.1[a] 400 g | nd (Morton) | 5,000[c] | 78.4 | 19.3 |
| 9.2[b] 400 g | 270 (Morton) | 5,000[d] | 91.1 | 4.7 |

[a]The concentration of hydrazine/CH$_2$Cl$_2$ mixture is 28% (v/v)
[b]The concentration of hydrazine/CH$_2$Cl$_2$ mixture is 14% (v/v).
[c]The Initial volume/reactor size was 21%. Final liquid volume/reactor size was 47%.
[d]The Initial volume/reactor size was 39%. Final liquid volume/reactor size was 64%.

The following conditions ensure a low level of the bis-hydrazide by-product is formed and are recommended for the manufacturing of p-methoxybenzylthioether hydrazide. These reaction conditions are considered aspects of certain embodiments of the present invention:

1. Addition rate of methoxybenzylthio acid chloride solution to hydrazine/CH$_2$Cl$_2$ mixture adjusted to maintain reaction temperature of −68 to −75° C.
2. Effective mixing (initial liquid volume of 30 to 40% liquid volume versus reactor size) at high mixing speed (300 to 400 rpm). Mixing maintained at speed of 260-270 rpm in 5 L Morton-type flask.
3. Stirrable, uniform mixture of hydrazine/CH$_2$Cl$_2$ (concentration was 5 to 19%, v/v). In one example the ratio of hydrazine/CH$_2$Cl$_2$ was 14%, v/v.
4. Initial liquid volume of 30 to 40% liquid volume versus reactor size.

The following examples 11-15 combine to illustrate a preferred embodiment of the invention.

Example 11

Modified Preparation of the p-Methoxybenzylthioether Acid Intermediate (1)

A 5-L reaction flask with a condenser, N$_2$ inlet, stirrer, and temperature probe/controller was set up. Piperidine (0.402 kg) was charged into the vessel under a $N_2$ atmosphere. 3,3-dimethylacrylic acid (0.215 kg) was added portion wise with stirring followed by p-methoxybenzylthiol (0.358 kg). The reaction mixture was heated gradually to 82 to 88° C. over a minimum of 15 minutes and that reaction temperature was maintained until an exotherm was observed. The temperature was not allowed to exceed 95° C. When the exotherm was complete, heating was continued to 92 to 98° C. and maintained for a minimum of 15 hours.

Three liters of 3 M aqueous HCl were prepared. The heating mantle was removed and the reaction mixture was allowed to cool to 70 to 75° C. 1.9 L of the HCl solution was slowly added. Cooling was continued with a water bath until the flask contents reached a temperature of 20 to 30° C. $CH_2Cl_2$ (1.64 kg) was added and the flask contents were stirred for a minimum of 5 minutes. The pH was checked and adjusted to <2 as needed using the HCl solution. The reaction mixture was transferred to a separatory funnel, the phases were allowed to separate, and the lower organic product layer was drained back into the reaction flask. The upper aqueous layer was transferred to a separate flask. The remaining HCl solution was added to the organic phase and stirred for a minimum of 5 minutes. The pH was checked and adjusted to <2 as needed with fresh 3 M HCl solution.

The contents of the reaction flask were returned to the separatory funnel and the layers were allowed to separate for a minimum of five minutes. The lower organic phase was drained to a clean Erlenmeyer flask and the aqueous layer was drained to the reaction flask. The aqueous phase from the previous extraction was added to the reaction flask as well as $CH_2Cl_2$ (0.400 kg). The reaction was stirred for a minimum of 5 minutes, then the contents of the reaction flask were transferred to the separatory funnel and the layers were allowed to separate for a minimum of five minutes. The lower organic product phase was combined with the previous organic product phase and transferred to the reaction flask. The combined aqueous phases were discarded as waste. Water (1.00 kg) was charged to the reaction flask and stirred for a minimum of 5 minutes. The mixture was transferred to the separatory funnel and the phases were allowed to separate for a minimum of five minutes. The lower product organic phase was drained to a clean Erlenmeyer flask. The aqueous phase was discarded as waste. The organic product solution was dried over anhydrous $MgSO_4$, then suction filtered into a 5-L 4-necked flask.

The Erlenmeyer flask and filter cake were rinsed into the 5-L 4-necked flask with $CH_2Cl_2$ (0.350 kg). $CH_2Cl_2$ was distilled off to a pot volume of 900±50 mL. The temperature of the concentrate was adjusted to 15 to 20° C. and then precipitated by adding heptane (1.67 kg). The mixture was cooled to about 5° C. and stirred for a minimum of 30 minutes, then the batch was suction filtered and the product cake rinsed with heptane (2×0.272 kg). The product was sampled for loss on drying analysis (LOD) and the filtrate sampled for Solids Content Projection. If the filtrate contains >0.110 kg, then it is concentrated and treated with heptane to precipitate a second crop of the product as before. The damp product cake(s) were weighed and the dry weight calculated using the LOD data. The dry mass of the product was equivalent to a constant A (kg). The damp product was returned to the 5-L flask and dissolved in $CH_2Cl_2$ (1.76×A kg minimum, 2.20×A kg maximum). Heptane was added (4.56×A kg) slowly, initiating precipitation. The slurry was cooled to 0 to 5° C. then aged for a minimum of 30 minutes. The batch was suction filtered and the product cake rinsed with heptane (2 portions, each 0.272 kg). Filtration was continued until filtrate flow essentially stopped. The wet product cake was transferred to a tared dish(es), a weight was obtained, then the filtrates were transferred to an appropriate waste container. The cake was dried in a vacuum oven at not more than 38° C. until a loss on drying LOD spec. of <1.0% was met. The sample was submitted for analysis.

Example 12A

Preparation of the p-Methoxybenzylthioether Acid Chloride (2)

A 5-L reaction flask equipped with a condenser, water scrubber, temperature probe, 1-L addition funnel, $N_2$ inlet, and stirrer was set up. $CH_2Cl_2$ (1.6 kg) was charged under a $N_2$ atmosphere followed by p-methoxybenzylthioether acid (0.400 kg) with stirring. A solution of oxalyl chloride (0.220 kg) and $CH_2Cl_2$ (0.600 kg) was prepared in the addition funnel. About half of the oxalyl chloride solution was added while maintaining a temperature range of 20 to 30° C. (exothermic!). $CO_2/CO$ evolution was observed while stirring for a minimum of 30 minutes, then the remaining oxalyl chloride solution was added, while maintaining the temperature between 20 and 30° C. The reaction was stirred until gas evolution diminished (about 30 min), then the mixture was heated to 33 to 38° C. This temperature was maintained for about 60 minutes until gas evolution diminished. The reaction was sampled, and HPLC was used to determine the amount of acid remaining. The reaction was judged complete when the amount of starting material was not more than 5%. If the reaction was not complete, then stirring was continued at 33 to 38° C. for an additional hour, then sampled and tested again. The heating mantle was removed and the reaction mixture was allowed to cool to 20 to 30° C. The mixture was transferred to a 3-L single-necked flask, then rinsed in with $CH_2Cl_2$. The batch was concentrated on a rotary evaporator until most of the volatiles were removed.

Example 12B

Preparation of the p-Methoxybenzylthioether Hydrazide Intermediate (3)

A 5-L 4-necked Morton type reaction flask with condenser, $N_2$ inlet, thermocouple, stirrer, and 2-L addition funnel was set up. $CH_2Cl_2$ (2.40 kg) was charged under a $N_2$ atmosphere and cooled to −75 to −65° C. Anhydrous hydrazine (0.252 kg) was charged to give a uniform slurry of hydrazine ice, without formation of hydrazine crystals on the sidewalls of the flask. The thioether acid chloride solution was transferred to the addition funnel, rinsing in $CH_2Cl_2$ as necessary to give a solution volume of 1.30 L.

The acid chloride solution was added drop wise at a steady rate over a minimum of three hours while maintaining the temperature between −65 to −75° C. (preferably between −70 to −75° C.). After the addition was complete, the reaction was stirred at −65 to −75° C. for a minimum of 30 minutes. The batch was warmed to 20 to 25° C. The reaction was sampled by HPLC and was judged complete if the amount of remaining acid chloride was not more than 5%. If the reaction was incomplete at this point, stirring was continued at 20 to 25° C. for a minimum of one hour, then sampled again. The batch in a 3-L flask was concentrated on the rotary evaporator. The batch was rinsed into the flask with $CH_2Cl_2$ as required. The concentrate was diluted with MeOH (1.25 kg) and transferred to a 5-L reaction flask equipped with stirrer, thermocouple, and $N_2$ inlet, rinsed in with MeOH as needed.

A solution of NaOH (0.0640 kg) in MeOH (1.25 kg) was added under a $N_2$ atmosphere and stirred for a minimum of 20 minutes. The batch was clarified by suction filtration and rinsed as required with MeOH. The filtrate was transferred to a tared 3-L flask (rinsed in with MeOH as required) and concentrated on the rotary evaporator until all of the volatiles were removed, then continued in vacuo for a minimum of 30 minutes. Application of vacuum was discontinued and $CH_2Cl_2$ (0.704 kg) was added. Rotation was continued to effect dissolution of the concentrate, then the application of vacuum was resumed and concentrated to a solid residue. The weight of the residue was obtained and the residue was transferred to a separatory funnel using $CH_2Cl_2$ (2.84 kg). The mixture was agitated to give a solution.

The $CH_2Cl_2$ solution was washed with two portions of water (1.00 kg each). Anhydrous $MgSO_4$ (0.300 to 0.420 kg) was added to the $CH_2Cl_2$ solution and swirled for about fifteen minutes until the solution was clear. The batch was suction filtered, rinsing with $CH_2Cl_2$ as required. The filtrate was transferred to a tared 3-L flask and concentrated on a rotary evaporator to a solid residue. The weight of the residue was obtained, and it was dissolved in $CH_2Cl_2$ (not less than 0.532 kg). The solution was transferred to a 1-L addition funnel that was attached to a 12-L 4-necked reaction flask equipped with a stirrer, thermocouple, and $N_2$ inlet. Ether (3.04 kg) was charged to the flask under a $N_2$ atmosphere. The ether was cooled to 0 to $-10°$ C.

The p-methoxybenzylthioether hydrazide solution was added to the rapidly stirring ether solvent while maintaining the temperature between $-10$ and $0°$ C. Additional solution was rinsed into the flask using $CH_2Cl_2$ (0.0660 kg). Heptane (0.732 kg) was charged to the addition funnel and was added slowly to the thin slurry, again maintaining the same temperature range. The resulting slurry was stirred at the same temperature for a minimum of 60 minutes. The batch was suction filtered through paper. The product cake was rinsed with heptane (2 portions, each 0.366 kg) and suction dried until a wet cake formed. The wet cake was transferred to tared dishes and the weight of the cake was obtained. The cake was dried in a vacuum oven (not more than 38° C.) until LOD was not more than 2.0%. The weight of the dried p-methoxybenzylthioether hydrazide was obtained and samples were submitted for testing.

Example 13

Preparation of Thiol-deprotected Intermediate (4)

Dowex SRB OH anionic exchange resin was prepared by adding 2.4 kg of the resin to a large Büchner funnel and washing with water (4 portions, each 2.40 kg) then MeOH (4 portions, each 1.92 kg). The resin was covered with water in a beaker and soaked for a minimum of one hour, then the water was filtered off. The resin was transferred to an appropriate storage container. A 5-L reaction flask equipped with a stirrer, thermocouple, $N_2$ inlet, and a 250 mL addition funnel was set up. Trifluoroacetic acid (2.80 kg) was charged under a $N_2$ atmosphere and cooled to 5 to 10° C. Thioether hydrazide (0.380 kg) was added portion wise (exothermic!), while maintaining the temperature between 5 and 15° C. The solution was cooled to 0 to 5° C.

Trifluoromethanesulfonic acid (0.243 kg) was charged to the addition funnel and added to the reaction mixture, while maintaining the temperature between 0 to 10° C. After the addition was complete, anisole (0.0152 kg) was added. The reaction mixture was stirred at 10 to 15° C. for a minimum of two hours or until the reaction color was deep red and did not change further. The reaction was sampled and tested by TLC and judged complete if the reaction mixture contained not more than 4% starting material. A 12-L reaction flask equipped with a stirrer, $N_2$ inlet, and 2-L addition funnel was set up. MeOH (3.01 kg) was charged. The vessel was cooled to 0 to 5° C. under a $N_2$ atmosphere. The reaction mixture was transferred to the addition funnel and then added to the chilled MeOH at a moderate rate, maintaining a reaction temperature of 0 to 5° C. A white precipitate formed. The reaction flask was rinsed into the addition funnel with additional MeOH (0.0790 kg). The white slurry was stirred for about 15 minutes at 0 to 5° C. The batch was suction filtered through paper and the product cake was rinsed with MeOH (2 portions, each 0.600 kg). After filtrate flow through the cake had essentially stopped, the filtrate was transferred to a tared 3-L flask (rinsed in with MeOH as required) and concentrated on the rotary evaporator to a semi-solid residue.

The residue was redissolved in MeOH (0.600 kg) and concentrated again as before. The residue was redissolved in $CH_2Cl_2$ (0.600 kg), concentrated again as before and the weight of the residue was obtained. The residue was dissolved in water (1.52 kg) and the solution was transferred to a 6-L separatory funnel. The residue was washed with $CH_2Cl_2$ (three portions, each 0.927 kg). The combined organic phases were transferred to an appropriate waste container. The aqueous phase containing the product was transferred to a beaker and the pH was adjusted to 6.5 to 7.5 pH units by addition of the swelled resin. The pH was adjusted with trifluoroacetic acid as necessary. Once the desired pH range was achieved, the slurry was stirred for about 30 minutes, and the pH was checked again, and adjusted if necessary. The batch was suction filtered and the resin was rinsed with water (2 portions, each 0.600 kg). 37% HCl solution (0.160 kg) was added. The pH was measured to ensure that it was <1.5. Additional HCl was added if necessary. The aqueous solution was transferred to a tared 3-L flask (rinsed in with water as required) and concentrated to a solid residue on the rotary evaporator. The weight of the residue was obtained. The residue was dissolved in absolute EtOH (1.20 kg) and concentrated again. The residue was re-dissolved in absolute EtOH (1.65 to 2.85 kg) and heated to 50 to 65° C. The warm solution was suction filtered. The filtrate was transferred to a tared 3-L flask and the ethanol solution concentrated on a rotary evaporator until distillation essentially ceased. EtOAc (8.21 kg) was charged in portions and concentrated as before. A fourth portion of EtOAc (2.74 kg) was charged and cooled to 20 to 25° C. Reaction was stirred for about 15 minutes. The batch was suction filtered and rinsed with EtOAc (2 portions, each 0.135 kg). Suction was continued until the filtrate flow essentially stopped. The cake was suction dried for about 60 minutes. The filtrate was discarded.

The weight of the damp product cake was obtained and that mass (kg) was used in subsequent calculations as a constant B. The product was transferred to a 12-L reaction flask equipped with a condenser, stirrer, $N_2$ inlet, and thermocouple. EtOAc (45.1×B kg) was charged under $N_2$ and the slurry heated to 48 to 53° C. with stirring. Heating was discontinued upon reaching 50° C. The heating mantle was removed and the slurry was cooled to 20 to 25° C. The batch was suction filtered and rinsed with EtOAc (2 portions, each 0.270 kg). Suction was continued until the filtrate flow essentially stopped. The filter cake was dried in a vacuum oven at not more than 38° C. for a minimum of 12 hours. The filter cake weight was obtained and the product mass (kg), equivalent to a constant C, was used in subsequent calculations.

Example 14

Preparation of Freebase Hydrazide (5)

The crude hydrochloride salt product (4) was mixed with water (20.0×C kg) in a 12-L 4-necked reaction flask and stirred to give a solution. The pH of the solution was adjusted with the treated resin until a range of 6.5 to 7.5 pH units was achieved. The batch was stirred for about 15 minutes, then the pH again was checked again and adjusted as needed to obtain a value of 6.5 to 7.5 pH units. The batch was suction filtered and rinsed with water (3.00×C kg), then with absolute EtOH (2 portions, each 5.30×C kg). Suction filtration was continued until filtrate flow essentially stopped. The product filtrate was transferred to a tared 3-L flask and rinsed in with absolute EtOH as required. The batch was concentrated on the rotary evaporator until distillation essentially stopped. The product residue was re-dissolved in absolute EtOH (1.58×C kg) and concentrated as before. The product residue was re-dissolved in anhydrous ether (2.57×C kg) and concentrated as before. Once distillation essentially stopped, drying was continued with high vacuum and evaporation continued for a minimum of two hours. The net weight of the residue was a constant D. The concentrate was transferred to a 12-L reaction flask equipped with a stirrer assembly, temperature probe, and nitrogen inlet using $CH_2Cl_2$ (66.3×D kg). The mixture was stirred at 15 to 30° C. for a minimum of 30 minutes. The batch was filtered, collecting the filtrates in a second 12-L reaction flask. The first flask was rinsed to the second flask through the filter using $CH_2Cl_2$ (3.98×D kg). The second flask containing the batch was equipped with a stirrer assembly, temperature probe, and nitrogen inlet. Silica gel (0.700×D kg) was charged with stirring and the stirring continued for about 30 minutes. The batch was suction filtered and the silica was washed with $CH_2Cl_2$ (2 portions, each 3.98×D kg), collecting the combined filtrates in a 10-L suction flask. The batch was concentrated on a rotary evaporator into a 1-L flask at about 30° C. The 10-L flask was rinsed to the evaporator as required with $CH_2Cl_2$. Distillation was continued until it essentially stopped. The rotary evaporator was switched to a high vacuum source and evaporation continued about three hours at 35 to 40° C.

The product oil crystallized by adjusting the rotary evaporator bath to 0 to 5° C. while rotating the flask at the maximum rate. Evaporation was continued for about 30 minutes after the product solidified. The free base product (5) was sampled and tested for residual methylene chloride and dried until the test for residual solvent was acceptable. The final weight was obtained, the product packaged in amber glass bottles with caps having inert liners, and samples submitted for testing. Yield The overall yield limit for the 5-step process is not less than 33% of theory (0.105 kg) and the difference between the highest and lowest yield must be not greater than 15%. The limit for the former process was 33 to 43% of theory; however, it is expected that the reduction in by-product formation afforded by the increase in methylene chloride in the hydrazide formation reaction will cause an increased yield. The actual yields in the validation batches will be used to define a yield range for production batches.

Example 15

Final Purification of 3-Methyl-3-Mercaptobutanoic Acid Hydrazide, Cl-332258 (DMH Linker)

Methylene chloride (1,000 mL, 1,325 g) was charged to a 2 L, 4-necked reaction flask equipped with a mechanical stirrer, $N_2$ inlet, reflux condenser, and temperature control device. DMH linker (20 g) was charged to a reaction flask. Under $N_2$, the slurry was stirred at 20±3° C. for a minimum of 30 minutes. The resulting cloudy solution of DMH linker was filtered through a 350 mL, medium sintered glass Buchner funnel. The filtrate was collected in a clean 2 L, 4-necked round bottom flask equipped with a mechanical stirrer, $N_2$ inlet, reflux condenser, and temperature control device. The reaction flask was rinsed to the clean reaction flask with 20 mL, 26.5 g methylene chloride. Silica gel (20 g) was charged to the solution in the reaction flask while maintaining temperature at 15-25° C. The slurry was stirred under $N_2$ at 20±3° C. for a minimum of 30 minutes. The heterogeneous mixture was filtered through a (350 mL, medium) sintered glass Buchner funnel. The filtrate was collected in a clean 2 L single necked round bottom flask. The reaction flask was rinsed to the filter cake with methylene chloride (50 mL, 66.3 g), collecting filtrate in single necked flask. The filtrate was concentrated to dryness using a rotary evaporator (bath=35±5° C.) and a mechanical water aspirator 15-30 mm Hg, followed by high vacuum (7-10 mm Hg). The resulting white solid was cooled to 0-5° C. and dried under high vacuum at 7 mm Hg for 2 hours. n-Heptane (100 mL, 68.4 g) was charged to the hard solid and stirred at room temperature for a minimum of 10 minutes until a uniform suspension was obtained.

The product was isolated by suction filtration through filter paper (#1 Whatman) on a 15 cm Buchner funnel. The 2 L flask was rinsed to the filtercake with the n-heptane mother liquors, followed by 2×50 mL, 2×34.2 g n-heptane washes. The filtercake was dried with suction at room temperature for a minimum of 5 minutes. The filtercake was transferred to an amber bottle placed in a vacuum desiccator and the damp cake was dried 14.34 g to constant weight in vacuo (<10 mm Hg) at 20-25° C. for 3 hours. Yield: 14.21 g. 75.9%, theoretical yield: 18.7 g.

| Test | Method | Tentative Limit | Found |
|---|---|---|---|
| Strength | HPLC, L18284-154 | 95% | 102.8% |
| Purity | HPLC, L18284-148 | 5% | 1.34% |
| Largest Single Imp. | HPLC, L18284-148 | 5% | 1.03% |
| Melting Point | USP | TBD | 51.5-52° C. |

We claim:

1. A method of preparing a hydrazide from hydrazine and an acyl halide comprising the steps of:
    (a) preparing a slurry comprising hydrazine and an inert solvent; and
    (b) adding an acyl halide continuously to said slurry, wherein the acyl halide further comprises a protected thiol.

2. The method according to claim 1 wherein the acyl halide is added substantially drop wise to the slurry.

3. The method according to claim 1 wherein the acyl halide comprises a benzyl thioether.

4. The method according to claim 1 wherein the acyl halide has the structure:

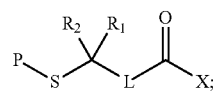

wherein P is a thiol protecting group;
$R_1$ and $R_2$ are each selected from the group consisting of $C_1$-$C_5$ alkyl;
X is a halide; and
L is an alkylene linker.

5. The method according to claim 4 wherein L is —$CH_2$—.

6. The method according to claim 4 wherein $R_1$ and $R_2$ are each independently methyl.

7. The method according to claim 4 wherein P is a benzyl group, optionally substituted on the phenyl ring.

8. The method according to claim 7 wherein P is p-methoxybenzyl group.

9. The method according to claim 1 wherein the acyl halide has the structure:

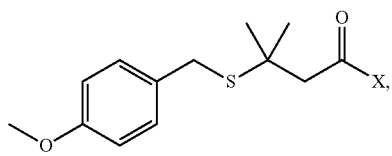

wherein X is a halide.

10. The method according to claim 1 wherein the inert solvent is methylene chloride.

11. The method according to claim 1 wherein said hydrazide product has the structure:

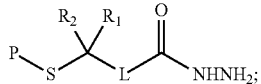

wherein P is a thiol protecting group;
$R_1$ and $R_2$ are each selected from the group consisting of $C_1$-$C_5$ alkyl; and
L is an alkylene linker.

12. The method according to claim 11 wherein L is —$CH_2$—.

13. The method according to claim 11 wherein $R_1$ and $R_2$ are each independently methyl.

14. The method according to claim 11 wherein P is a benzyl group, optionally substituted on the phenyl ring.

15. The method according to claim 14 wherein P is p-methoxybenzyl group.

16. The method according to claim 11 wherein the hydrazide product is

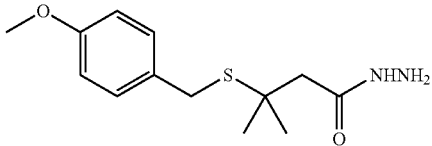 [SMILES: COc1ccc(CSC(C)(C)CC(=O)NN)cc1]

or a salt thereof.

17. The method according to claim 1 wherein the hydrazide contains less than 5% of a bis-hydrazide by-product having the structure:

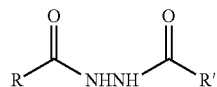

wherein R and R' are optionally substituted alkyl, heteroalkyl, or heteroalkaryl groups.

18. The method according to claim 17 wherein R and R' are

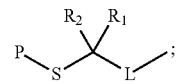

wherein P is a thiol protecting group;
$R_1$ and $R_2$ are each selected from the group consisting of $C_1$-$C_5$ alkyl; and
L is an alkylene linker.

19. The method according to claim 18 wherein L is —$CH_2$—.

20. The method according to claim 19 wherein $R_1$ and $R_2$ are each independently methyl.

21. The method according to claim 18 wherein P is a benzyl group, optionally substituted on the phenyl ring.

22. The method according to claim 21 wherein P is p-methoxybenzyl group.

23. The method according to claim 22 wherein the bis-hydrazide by-product has the structure:

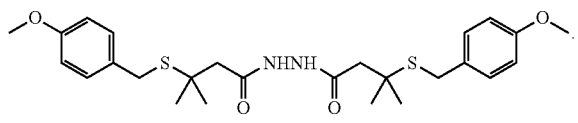

24. The method according to claim 1 wherein the continuous addition of acid halide solution is adjusted to maintain reaction temperature of about −68° C. to about −75° C.

25. A method of preparing 3-methyl-3-mercaptobutanoic acid hydrazide comprising the step of preparing a hydrazide according to the method of claim 15.

26. A method of preparing an immunoconjugate of a member of the family of calicheamicins with a monoclonal antibody as carrier, which comprises preparing 3-methyl-3-mercaptobutanoic acid hydrazide according to the method of claim 25 and using the 3-methyl-3-mercaptobutanoic acid hydrazide for preparing said immunoconjugate.

27. The method according to claim 26 wherein 3-methyl-3-mercaptobutanoic acid hydrazide is used as a linker to make gemtuzumab ozogamicin or inotuzumab ozogamicin.

28. A method of preparing gemtuzumab ozogamicin comprising the steps of preparing the linker 3-methyl-3-mercaptobutanoic acid hydrazide according to the method of claim 25 and using said linker to link calicheamicin to the monoclonal antibody gemtuzumab.

* * * * *